(12) United States Patent
Harwood et al.

(10) Patent No.: US 12,115,313 B2
(45) Date of Patent: *Oct. 15, 2024

(54) RESPIRATORY INTERFACE

(71) Applicant: Fisher & Paykel Healthcare Limited, Auckland (NZ)

(72) Inventors: Jonathan David Harwood, Auckland (NZ); Christopher Earl Nightingale, Auckland (NZ); Gregory James Olsen, Auckland (NZ); Craig Robert Prentice, Auckland (NZ); Daniel John Smith, Auckland (NZ); Brett John Huddart, Auckland (NZ); Andrew Paul Maxwell Salmon, Auckland (NZ); Olivia Marie Allan, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/807,092

(22) Filed: Jun. 15, 2022

(65) Prior Publication Data

US 2023/0084771 A1 Mar. 16, 2023

Related U.S. Application Data

(63) Continuation of application No. 16/820,417, filed on Mar. 16, 2020, now Pat. No. 11,389,610, which is a (Continued)

(51) Int. Cl.
*A61M 16/06* (2006.01)
*A61M 16/08* (2006.01)
(Continued)

(52) U.S. Cl.
CPC ........ *A61M 16/06* (2013.01); *A61M 16/0816* (2013.01); *A61M 16/0825* (2014.02);
(Continued)

(58) Field of Classification Search
CPC .. A61M 16/00; A61M 16/08; A61M 16/0816; A61M 16/0825; A61M 16/0875;
(Continued)

(56) References Cited

U.S. PATENT DOCUMENTS 3,295,529 A 1/1967 Corrigall et al.
3,824,999 A 7/1974 King
(Continued)

FOREIGN PATENT DOCUMENTS

DE 29723101 U1 7/1998
DE 10 2012 004359 9/2012
(Continued)

OTHER PUBLICATIONS

Quattro Air Headgear, Components Card, 2013.
Quattro Air Headgear, Fact Sheet, 2013.

*Primary Examiner* — Colin W Stuart
(74) *Attorney, Agent, or Firm* — Villamar & Guiliana LLP

(57) ABSTRACT

Interfaces for positive pressure therapy having a mask assembly, a headgear assembly and a connection port assembly are disclosed herein. The connection port assembly has a ball joint connection with the mask assembly and includes a quick release button for easily disconnecting the gases source conduit from the mask assembly. The mask assembly may include a bias flow vent that is formed separately and attached to the mask assembly. The headgear assembly encircles the rear region of the user's head and may include at least some portions that are substantially non-stretchable.

20 Claims, 20 Drawing Sheets

Related U.S. Application Data continuation of application No. 15/103,279, filed as application No. PCT/NZ2014/050021 on Dec. 11, 2014, now Pat. No. 10,828,454.

(60) Provisional application No. 61/914,635, filed on Dec. 11, 2013.

(51) Int. Cl.
| | |
|---|---|
| A61M 16/20 | (2006.01) |
| A61M 39/10 | (2006.01) |
| B29C 65/08 | (2006.01) |
| B29L 31/48 | (2006.01) |

(52) U.S. Cl.
CPC ..... *A61M 16/0875* (2013.01); *A61M 16/0616* (2014.02); *A61M 16/0633* (2014.02); *A61M 16/0683* (2013.01); *A61M 16/208* (2013.01); *A61M 39/10* (2013.01); *A61M 2039/1033* (2013.01); *A61M 39/1055* (2013.01); *A61M 2202/0225* (2013.01); *A61M 2205/42* (2013.01); *A61M 2207/00* (2013.01); *B29C 65/08* (2013.01); *B29L 2031/4835* (2013.01)

(58) Field of Classification Search
CPC .............. A61M 16/06; A61M 16/0605; A61M 16/0633; A61M 16/0638; A61M 16/0644; A61M 16/0683; A61M 16/20; A61M 16/205; A61M 2016/0661; A61M 2205/42; A61M 25/0014; A61M 25/0097; A61M 39/00; A61M 39/10; A61M 39/1055; A61M 2039/1033; F16L 27/04; F16L 27/073; F16L 27/08; F16L 27/0804; F16L 27/0845

See application file for complete search history.

(56) References Cited

U.S. PATENT DOCUMENTS

| | | | |
|---|---|---|---|
| 4,274,406 | A | 6/1981 | Bartholomew |
| 4,773,448 | A | 9/1988 | Francis |
| 4,938,209 | A | 7/1990 | Fry |
| 5,259,376 | A | 11/1993 | Bales |
| 5,918,598 | A | 7/1999 | Belfer |
| 5,921,239 | A | 7/1999 | McCall et al. |
| 6,581,594 | B1 | 6/2003 | Drew et al. |
| 6,631,718 | B1 | 10/2003 | Lovell |
| 6,662,803 | B2 | 12/2003 | Gradon et al. |
| 6,679,257 | B1 | 1/2004 | Robertson |
| 6,823,869 | B2 | 11/2004 | Raje |
| 6,892,729 | B2 | 5/2005 | Smith |
| 7,290,546 | B2 | 11/2007 | Sprinke |
| 7,487,772 | B2 | 2/2009 | Ging |
| 7,810,499 | B2 | 10/2010 | Janbakhsh |
| 7,823,589 | B2 | 11/2010 | Janbakhsh |
| 7,827,987 | B2 | 11/2010 | Woodard et al. |
| 7,861,715 | B2 | 1/2011 | Jones |
| 7,997,267 | B2 | 8/2011 | Ging |
| 8,479,736 | B2 | 7/2013 | Ging |
| 8,505,535 | B2 | 8/2013 | Jones |
| 8,535,771 | B2 | 9/2013 | Eifler |
| 8,887,726 | B2 | 11/2014 | Schulz |
| D751,188 | S | 3/2016 | Skipper et al. |
| D771,241 | S | 11/2016 | Skipper et al. |
| D795,417 | S | 8/2017 | Amarasinghe et al. |
| D810,277 | S | 2/2018 | Amarasinghe et al. |
| D855,794 | S | 8/2019 | Gray et al. |
| 10,727,454 | B2 | 11/2020 | Harwood et al. |
| 10,828,454 | B2 | 11/2020 | Harwood et al. |
| 11,389,610 | B2 * | 7/2022 | Harwood .......... A61M 16/0816 |
| 11,766,534 | B2 | 9/2023 | Harwood |
| 2003/0075180 | A1 | 4/2003 | Raje |
| 2003/0094177 | A1 | 5/2003 | Smith et al. |
| 2004/0045550 | A1 | 3/2004 | Lang |
| 2005/0012329 | A1 | 1/2005 | Brown |
| 2005/0076913 | A1 | 4/2005 | Ho |
| 2006/0076017 | A1 | 4/2006 | Walker et al. |
| 2006/0283458 | A1 | 12/2006 | Woodard et al. |
| 2007/0101998 | A1 | 5/2007 | Kwok et al. |
| 2007/0209663 | A1 | 9/2007 | Marque et al. |
| 2008/0060657 | A1 | 3/2008 | McAuley |
| 2008/0066745 | A1 | 3/2008 | Janbakhsh et al. |
| 2008/0210241 | A1 | 9/2008 | Schulz et al. |
| 2008/0276937 | A1 | 11/2008 | Davidson et al. |
| 2009/0044808 | A1 | 2/2009 | Guney et al. |
| 2009/0050156 | A1 | 2/2009 | Ng et al. |
| 2009/0065729 | A1 | 3/2009 | Warboys et al. |
| 2009/0223521 | A1 | 9/2009 | Howard et al. |
| 2010/0229866 | A1 | 9/2010 | Sullivan |
| 2010/0258133 | A1 | 10/2010 | Todd et al. |
| 2010/0307502 | A1 | 12/2010 | Rummery |
| 2011/0146685 | A1 | 6/2011 | Allan et al. |
| 2011/0197341 | A1 * | 8/2011 | Formica .................... B32B 5/18 2/209.3 |
| 2011/0232649 | A1 | 9/2011 | Callazo et al. |
| 2012/0067349 | A1 | 3/2012 | Barlow |
| 2012/0138061 | A1 | 6/2012 | Dravitzki |
| 2012/0285457 | A1 | 11/2012 | Mansour et al. |
| 2012/0318272 | A1 | 12/2012 | Ho |
| 2013/0131534 | A1 | 5/2013 | Heatherington |
| 2014/0150798 | A1 | 6/2014 | Fong et al. |
| 2014/0174446 | A1 | 6/2014 | Prentice |
| 2015/0059762 | A1 | 3/2015 | Schultz |
| 2015/0151071 | A1 | 6/2015 | Von Moger |
| 2015/0246198 | A1 | 9/2015 | Bearne |
| 2016/0045700 | A1 | 2/2016 | Amarasinghe |
| 2016/0213876 | A1 | 7/2016 | McAuley et al. |
| 2017/0296770 | A1 | 10/2017 | Gunaratnam et al. |
| 2020/0215289 | A1 | 7/2020 | Harwood |

FOREIGN PATENT DOCUMENTS

| | | |
|---|---|---|
| EP | 0 697 225 | 2/1996 |
| EP | 1 075 848 | 2/2001 |
| EP | 2 451 518 | 10/2017 |
| NO | 05/079726 | 9/2005 |
| WO | WO 05/021075 | 3/2005 |
| WO | WO 06/069415 | 7/2006 |
| WO | WO 10/131189 | 11/2010 |
| WO | WO 11/014931 | 2/2011 |
| WO | WO 12/024728 | 3/2012 |
| WO | WO 12/052902 | 4/2012 |
| WO | WO 12/140514 | 10/2012 |
| WO | WO 13/006899 | 1/2013 |
| WO | WO 13/170290 | 11/2013 |
| WO | WO 14/117227 | 8/2014 |
| WO | WO 00/74758 | 12/2020 |

\* cited by examiner

RESPIRATORY INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference in their entireties and made a part of the present disclosure.

BACKGROUND OF THE INVENTION

Field of the Invention

The present invention generally relates to face masks that cover at least one of a nose and a mouth of a user to supply respiratory gas under positive pressure. More particularly, certain aspects of the present disclosure relate to such masks that have a detachable ball joint, a separately formed bias flow vent and non-stretchable headgear.

Description of the Related Art

Face masks can be used to provide respiratory gases to a user under positive pressure. In configurations in which both a mouth and a nose of a user are covered, the full face mask typically will overlie a bridge of the nose. Generally, a single seal will circumscribe the nose and the mouth of the user.

Such full face masks commonly are secured to a head of the user with headgear. In order to sufficiently reduce leakage, the headgear typically is tightened, which results in an elevated pressure being exerted on a bridge of a user's nose. In other words, as the headgear is tightened, the silicone seal typically applies a progressively increasing load on the bridge of the nose. The pressure can be a source of discomfort and, in some circumstances, can lead to pressure sores over time.

SUMMARY OF THE DISCLOSURE

It is an object of the present disclosure to provide one or more constructions and/or methods that will at least go some way towards improving on the above or that will at least provide the public or the medical profession with a useful choice.

In accordance with at least one of the embodiments disclosed herein, a mask assembly can comprise a seal chamber configured to cover at least a mouth or a nose of a user, a mask frame, and a fluid connector configured to connect the mask assembly to a gases supply. The fluid connector can comprise a conduit with a first end and a second end. A passage extends from the first end to the second end for transporting gases therebetween. The fluid connector can comprise a releasable connection at the first end that is configured to couple to a ball joint.

In some configurations, the passage of the fluid connector can comprise a bend. The bend can have an angle ranging from about 30 degrees to approximately 150 degrees. In some configurations, the bend has an angle of about 90 degrees.

The releasable connection can comprise a quick release button. The quick release button can be overmoulded in the fluid connector. The quick release button can comprise a protrusion configured to engage a shoulder on the ball joint. In some configurations, the releasable connection comprises quick release buttons on opposite sides of the fluid connector and the releasable connection is actuated by squeezing the fluid connector.

In some configurations, the ball joint can be disposed on the seal chamber such that the fluid connector attaches to the seal chamber. In other configurations, the ball joint can be disposed on the mask frame such that the fluid connector attaches to the mask frame. The mask assembly can further comprise a sealing flap configured to at least partially seal the joint between the fluid connector and the ball joint.

In accordance with at least one of the embodiments disclosed herein, a fluid connector configured to connect a mask assembly to a gases supply can comprise a conduit comprising a first end and a second end. A passage can extend from the first end to the second end for transporting gases therebetween. A releasable connection can be disposed at the first end configured to couple to a ball joint.

In some configurations, the passage of the fluid connector can comprise a bend. The bend can have an angle ranging from about 30 degrees to approximately 150 degrees. In some configurations, the bend has an angle of about 90 degrees.

The releasable connection can comprise a quick release button. The quick release button can be overmoulded in the fluid connector. The quick release button can comprise a protrusion configured to engage a shoulder on the ball joint. In some configurations, the releasable connection comprises quick release buttons on opposite sides of the fluid connector and the releasable connection is actuated by squeezing the fluid connector.

In accordance with at least one of the embodiments disclosed herein, a mask assembly is provided comprising a seal chamber configured to cover at least a mouth or a nose of a user. The seal chamber can comprise a mask base comprising a passage that is configured to accept a gases supply connector, and a mask seal attached around a perimeter of the mask base and configured to form a seal against the user's face. The mask assembly can also comprise a mask frame and an air vent module comprising a plurality of vent holes. The air vent module can be a separate component that is attachable to the mask assembly.

In some configurations, the air vent module of the mask assembly has an annular shape and the plurality of vent holes are arranged in a circular configuration. The air vent module can be disposed around the passage. In some configurations, the air vent module is permanently overmoulded onto the mask assembly. The mask assembly can further comprise a flexible coupling between the air vent module and the mask assembly. In some configurations, the air vent module is attached to the seal chamber. In other configurations, the air vent module is attached to the mask frame.

In some configurations, the passage of the seal chamber can be configured to accept a ball joint.

The mask frame can comprise a flexible forehead rest. In some configurations, the mask frame is configured to be disposed around a perimeter region of the seal chamber.

In accordance with at least one of the embodiments disclosed herein, an air vent module is provided that is configured to couple to a respiratory mask assembly for venting exhaled gases to atmosphere. The air vent module can comprise one or more vent holes. The air vent module can be a separate component that is attachable to the mask assembly.

The air vent module can have an annular shape and the one or more vent holes can be arranged in a circular configuration. In some configurations, the air vent module can be configured to be permanently overmoulded onto the mask assembly. The air vent module can be attachable to a seal chamber of the mask assembly or a mask frame of the mask assembly.

In accordance with at least one of the embodiments disclosed herein, a method of manufacturing a mask assembly can comprise the steps of: providing one or both of a mask frame and a seal chamber configured to cover at least a mouth or a nose of a user; providing a separate air vent module, the air vent module comprising one or more vent holes; and coupling the air vent module to the seal chamber or mask frame.

The air vent module can have an annular shape and the one or more vent holes can be arranged in a circular configuration. In some configurations, the air vent module can be configured to be permanently overmoulded onto the seal chamber or mask frame. The mask frame can comprise a flexible forehead rest. The mask frame can be configured to be disposed around a perimeter region of the seal chamber.

In accordance with at least one of the embodiments disclosed herein, a headgear assembly can be configured to secure a mask assembly to a user's head. The headgear assembly can comprise a generally annular component comprising a back strap, a top strap and a pair of upright straps. The headgear assembly can further comprise a pair of upper side straps and a pair of lower side straps. The annular component can be substantially non-stretchable and configured to encircle the occipital region of a user's head.

The back strap, the top strap, the pair of upright straps, the pair of upper side straps and the pair of lower side straps can be at least partially coupled together using ultrasonic welding. In some configurations, the top strap is adjustable in length. The headgear assembly can be configured to directly couple to the mask assembly without the use of clips. In some configurations, the pair of upper side straps and the pair of lower side straps can comprise ends with fasteners that loop through headgear attachments on the mask assembly and the fasteners can be configured to couple with complementary fasteners on the sides of the pair of upper side straps and the pair of lower side straps.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Figure 1:
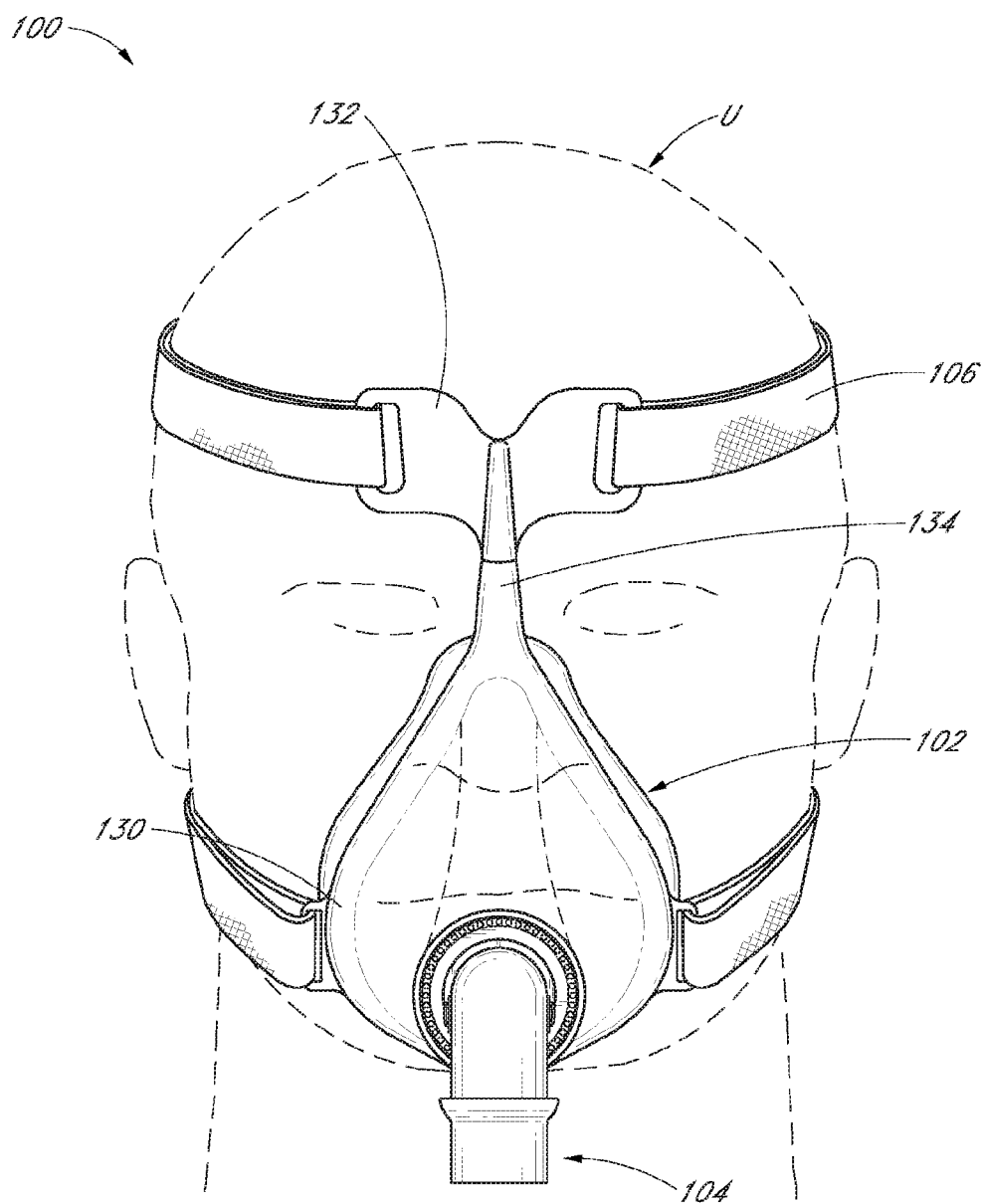
FIG. 1 is a front elevational view of a respiratory interface on a patient's head.
Figure 2:
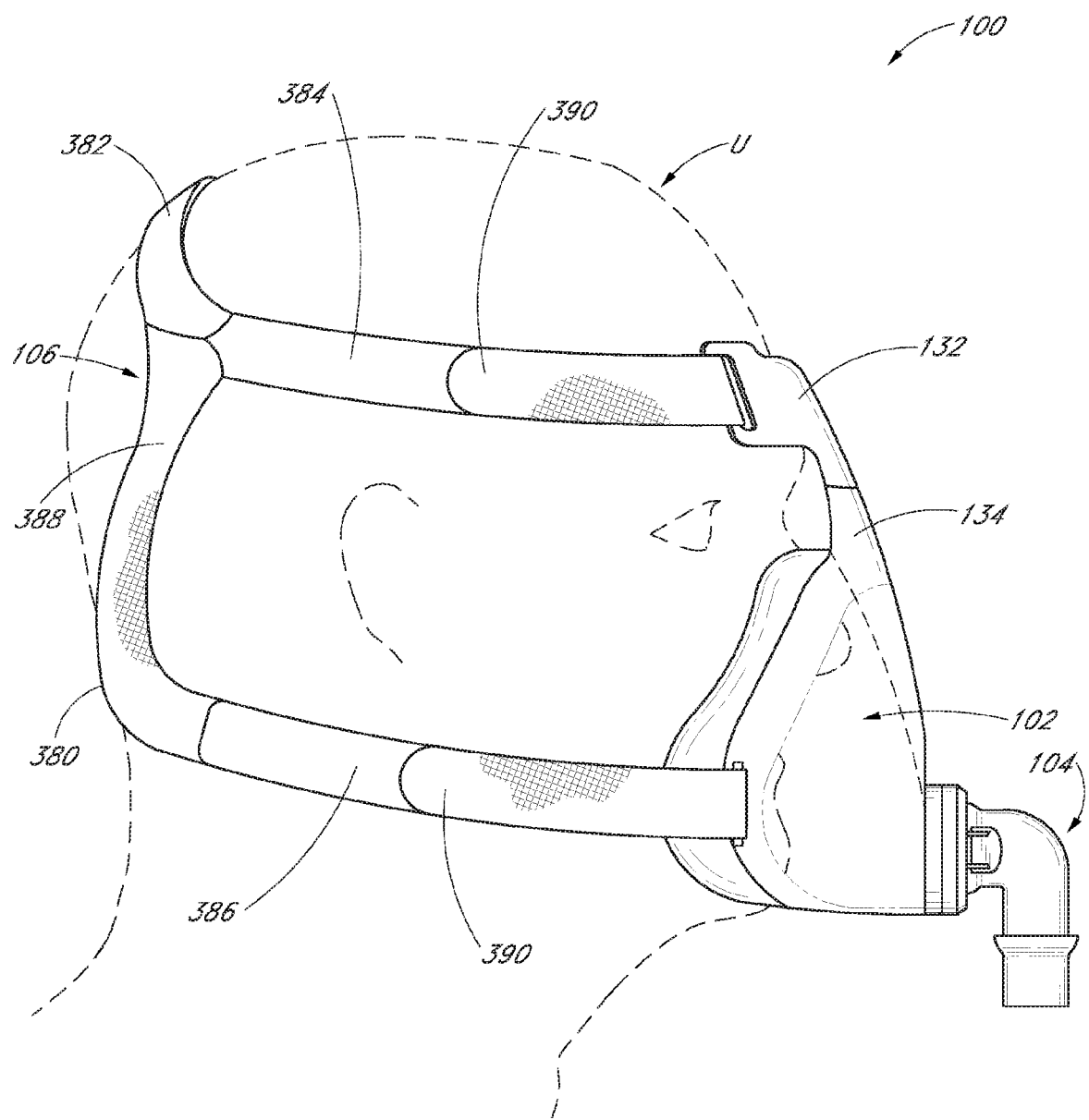
FIG. 2 is a side elevational view of the respiratory interface of FIG. 1 on a patient's head.

With reference initially to FIGS. 1 and 2, an embodiment of an interface 100 is illustrated coupled to a user U. The interface 100 can be used in the field of respiratory therapy. In some embodiments, the interface 100 has particular utility with forms of positive pressure respiratory therapy. For example, the interface 100 can be used for administering continuous positive airway pressure ("CPAP") treatments, variable positive airway pressure ("VPAP") treatments and/ or bi-level positive airway pressure ("BiPAP") treatments. The interface can be compatible with one or more different types of suitable CPAP systems.

The interface 100 can comprise any of a plurality of different types of suitable mask configurations. For example, certain features, aspects and advantages of the present invention can be utilized with nasal masks, full face masks, oronasal masks or any other positive pressure mask. Although the illustrated mask is a full face mask, the scope of the present disclosure should not be limited by the particular embodiments described. With continued reference to FIGS. 1 and 2, the interface 100 generally comprises a mask assembly 102, a connection port assembly 104 and a headgear assembly 106.

Figure 3:
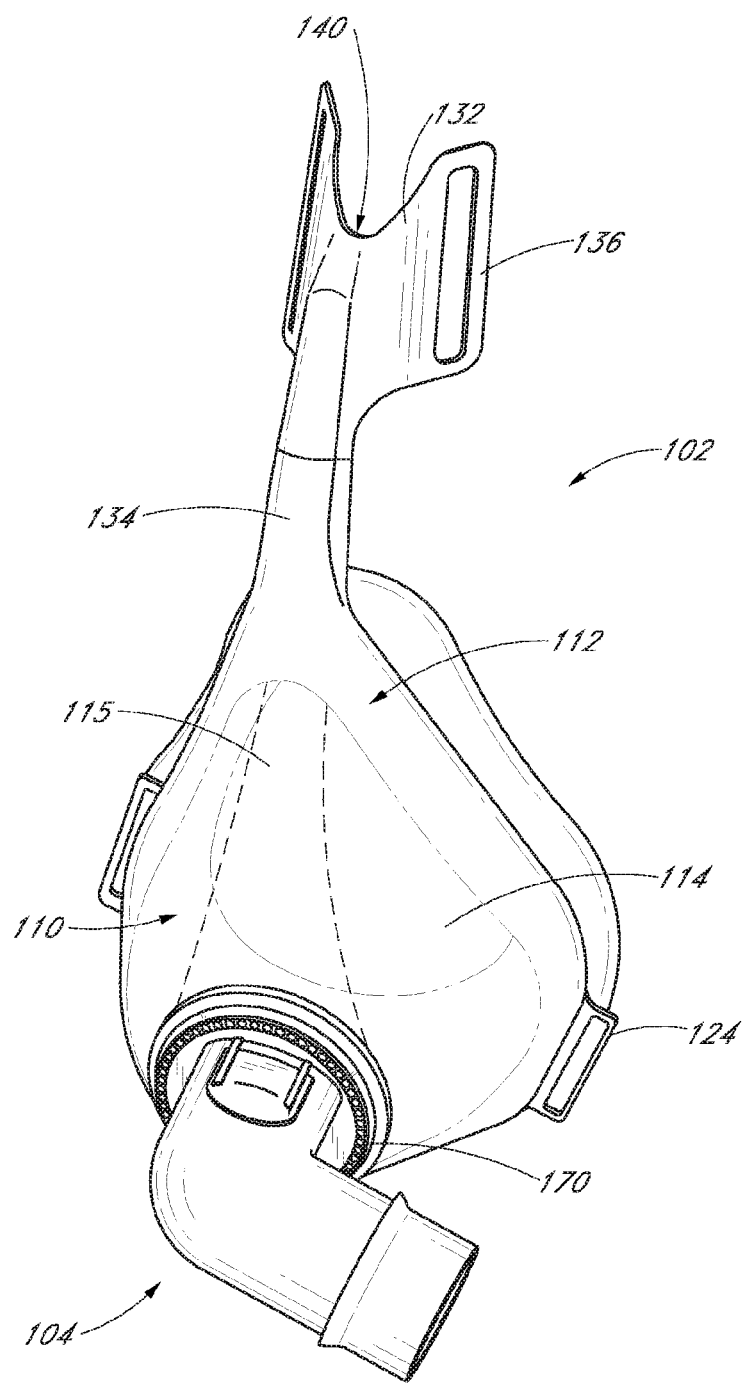
FIG. 3 is a top perspective view of the respiratory interface of FIG. 1.
Figure 4:
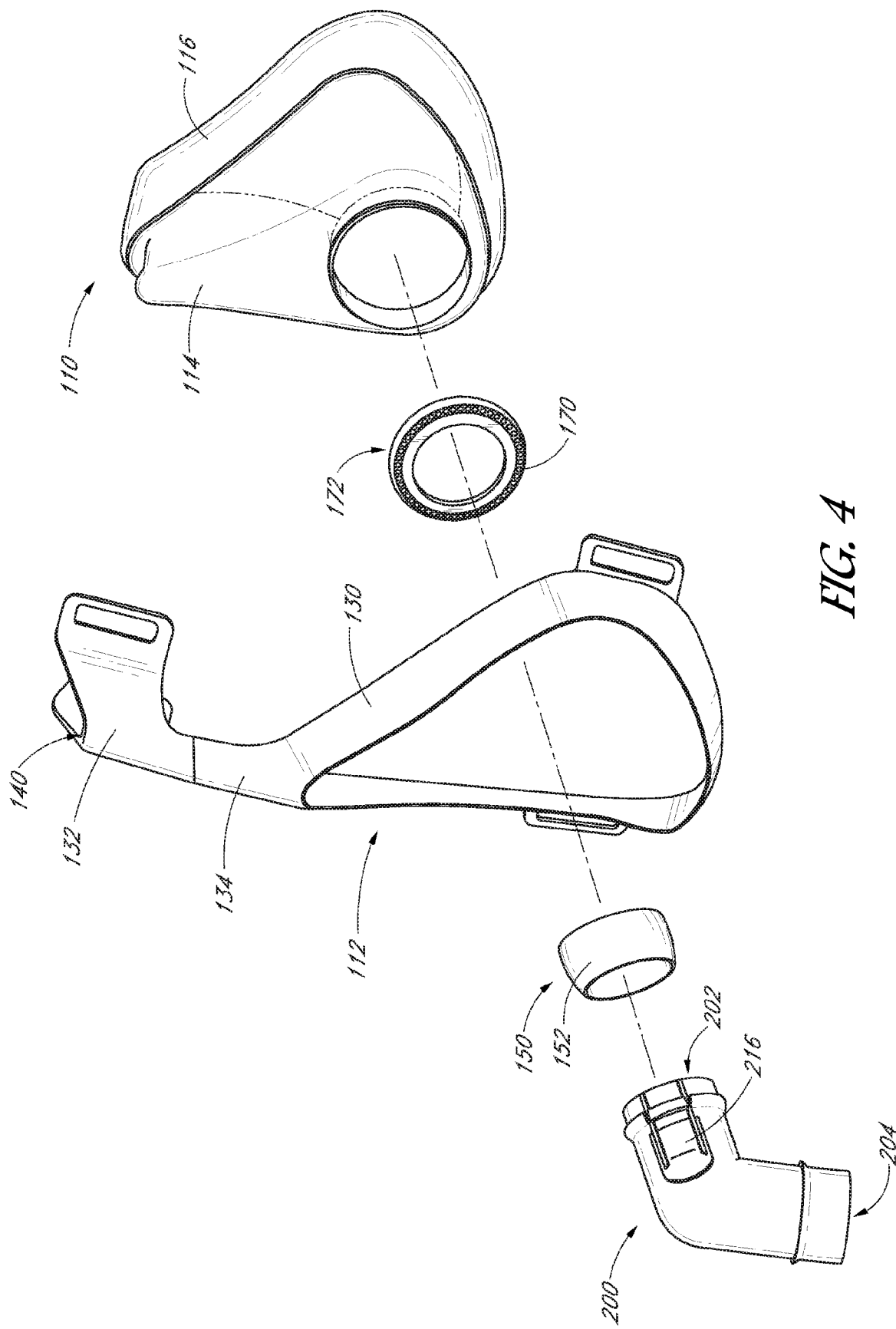
FIG. 4 is an exploded perspective view of the components of a respiratory interface.

With reference to FIGS. 3 and 4, the mask assembly 102 can include a seal chamber 110 and a mask frame 112. The seal chamber 110 is configured to cover the user's mouth and/or nose to deliver respiratory gases to the user. The seal chamber 110 can be secured by the mask frame 112. The mask frame 112 is held in place by a headgear assembly 106 that wraps around the user's head. A connection port assembly 104 can be releasably connected to the mask assembly 102, with a quick-release connection. A ball joint can be disposed between the connection port assembly 104 and seal chamber 110 to improve flexibility and comfort.

The mask frame 112 can couple to the seal chamber 110 to hold the seal chamber 110 and help stabilize the mask assembly 102 on the user's face. In the configuration illustrated in FIG. 4, the mask frame 112 has a frame loop 130 that extends generally around the perimeter of the seal chamber 110. In other configurations, the mask frame can be any shape and size to functionally secure the seal chamber to the user's face. The mask frame 112 can be attached to the seal chamber 110 with interlocking clips, tabs or other functional couplers. The mask frame 112 can be rigid, substantially rigid or semi-rigid to provide support for the seal chamber 110. For example, the mask frame 112 can be at least partially made of a metal or rigid plastic, such as acrylic or high-density polyethylene. The mask frame 112 and seal chamber 110 can be separate components or in an alternative embodiment the seal chamber and mask frame may be formed as a single component, including that the seal chamber may not have a distinct mask frame but may simply have integral headgear attachment parts that are configured to fasten with the headgear straps, which should be understood as a 'seal chamber and mask frame' as that terminology is used in this specification and claims.

As illustrated in FIGS. 1, 2 and 3 the mask frame 112 can include a forehead rest 132. The forehead rest 132 can help stabilize the interface 100 to the user's face by providing a support point for the mask assembly 102 and connection points for the headgear assembly 106. In the illustrated configuration, the forehead rest 132 is separated from the frame loop 130 by a bridge member 134 that extends from the top of the frame loop 130. The bridge member 134 can be integrally formed or molded with the frame loop 130 from the same rigid material.

The forehead rest 132 can be a separate flexible piece that is attached or overmoulded onto the mask frame 112. For example, the forehead rest 132 can be made of a flexible silicone that is overmoulded onto the bridge member 134. The flexible material advantageously conforms to the user's forehead anatomy and helps improve comfort to the user with soft material contact. In some configurations, the forehead rest 132 can be attached or integrally formed as part of the mask frame and can be made of the same material as the frame loop 130 and bridge member 134.

Figure 15:
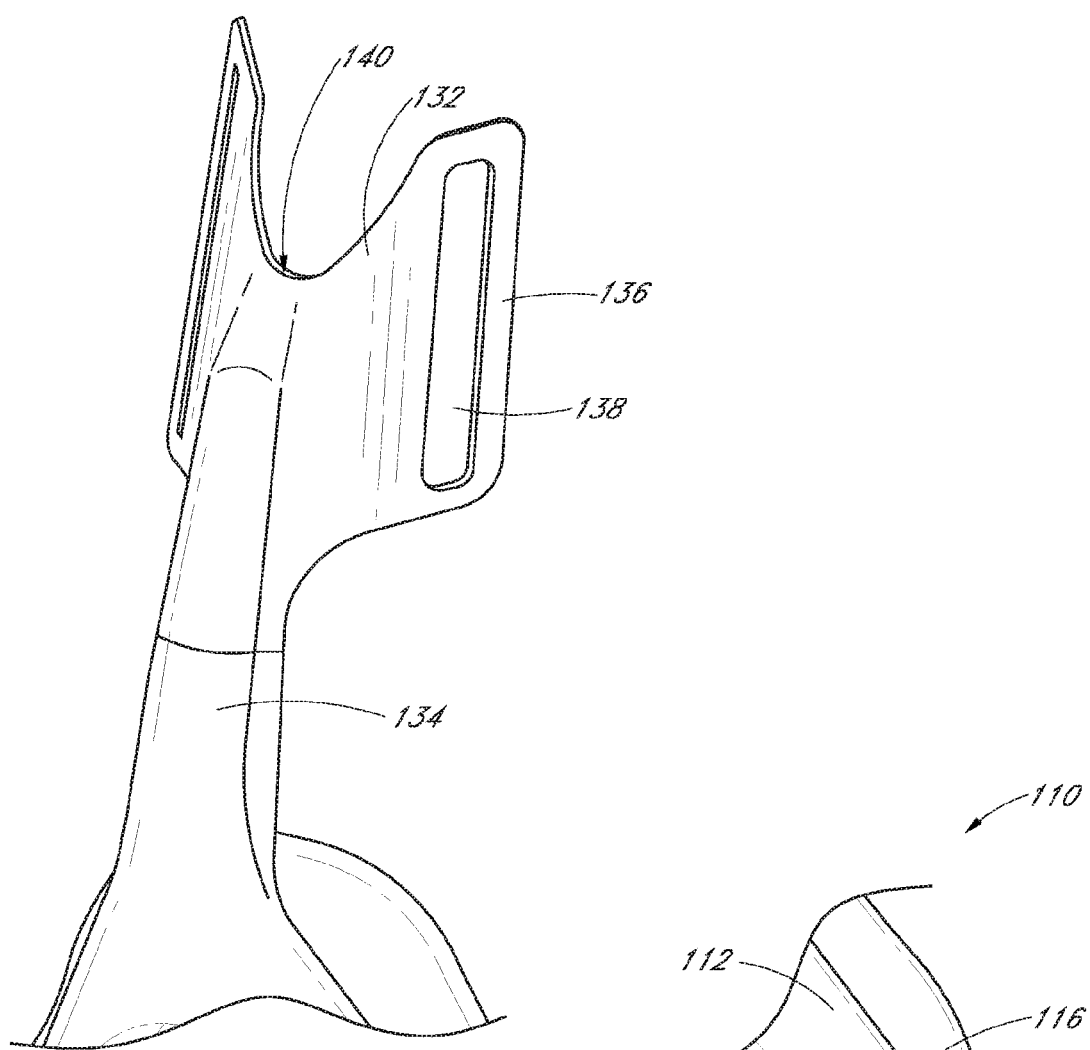
FIG. 15 is a close-up perspective view of a mask frame showing a headgear attachment.
Figure 16:
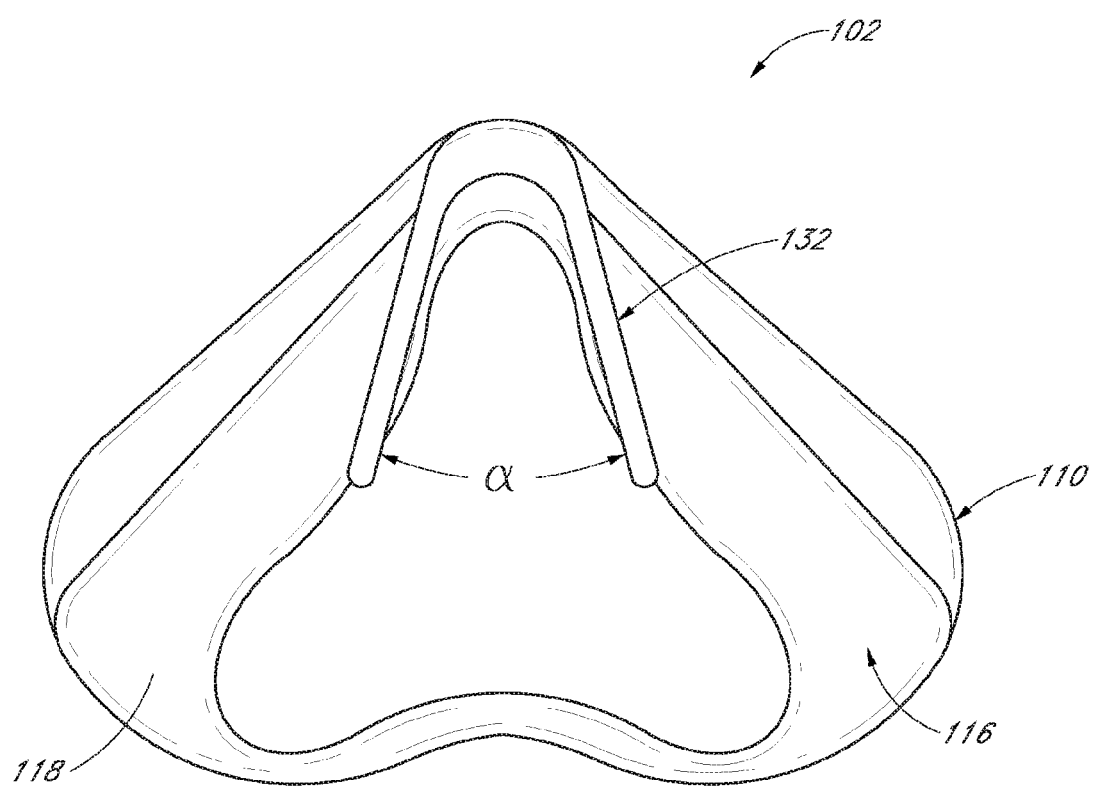
FIG. 16 is a top plan view of a mask assembly.

In some configurations, the forehead rest 132 can have a preformed V-shape when viewed from the top, as illustrated in the top plan view of the mask assembly in FIG. 16. The angle α between the sides of the forehead rest 132 can be any suitable angle. In some configurations, the angle α can be at least approximately 20 degrees and/or less than or equal to 180 degrees. With reference to FIG. 15, the sides of the forehead rest 132 can have headgear attachments 136 for coupling straps or connectors. The forehead rest 132 can at least partially flatten as the headgear tension pulls the sides of the forehead rest 132 apart, as illustrated in FIGS. 1 and 2. As the sides of the forehead rest 132 spread apart, the contact area with the user's forehead increases, spreading the pressure of the mask assembly and reducing discomfort from localized pressure areas. The flexibility of the forehead rest 132 and the amount that the V-shaped forehead rest 132 can be spread apart enables users to adjust how far off the face the mask frame 112 sits to enable customization for different facial geometries and improve comfort and performance.

As illustrated in FIGS. 3, 4 and 15, the forehead rest 132 can include a cutout 140 generally disposed on the top edge of the forehead rest 132. In the illustrated configuration, the cutout is generally U-shaped or V-shaped and extends down from the middle of the top edge. In other configurations, the cutout can have any suitable shape, such as square shaped or trapezoidal shaped. The cutout can advantageously improve the flexibility of the sides of the forehead rest 132 by providing stress relief as the sides are spread apart. Other advantages of the cutout can include reduced material costs and improved aesthetics of the forehead rest 132.

In some configurations, the forehead rest can be generally flat without a preformed V-shape. The generally flat forehead rest can be made of a soft material, as described for the V-shaped forehead rest, or harder material, such as the frame loop 130 and bridge member 134 material. The flat forehead rest can have any of a plurality of different shapes that help distribute the mask assembly load on the user's head, such as rectangular, square, T-shaped, oval, V-shape and the like.

For the user's comfort, one or more cushions can be provided underneath the forehead rest. The cushion can be constructed of silicon, foam or other material that provides cushioning.

In some embodiments, the bridge member 134 can be made of a flexible material to provide conformability to the user's anatomy. The bridge member can have a flexible insert that allows the bridge member to bend and return to its unstressed shape once forces are removed. For example, the bridge member can comprise a resilient metal strip overmoulded or otherwise attached to the bridge member. In other embodiments, the metal can be malleable to bend to a particular angle and have enough stiffness to retain the angle once coupled on the patient. Stiffness can be configured by choice and thickness of insert. In some embodiments, the bridge member can be made of a flexible material and the bending characteristics of the bridge member can be controlled by adjusting the thickness of the material. For example, the bridge member can be made of silicone, or like material, and be relatively thinner in the sagittal (forward-aft) direction and relatively thicker in the coronal (side-to-side) direction to predispose the forehead rest to bend in the sagittal direction. In some embodiments, the forehead rest 132 may include a weakened section at its base which allows the forehead rest 132 to pivot from the bridge member 134. The extent of flexibility of this joint can be varied by its thickness.

Preferably the insert displays a limited degree of work hardening over the range of plastic deformation. For example soft alloys are less likely to snap after a large amount of bending back and forwards. Alloys involving aluminium or copper are possible constructions. Portions of the insert, body and/or forehead rest may be encapsulated by a pliable material, such as silicone.

Figure 5:
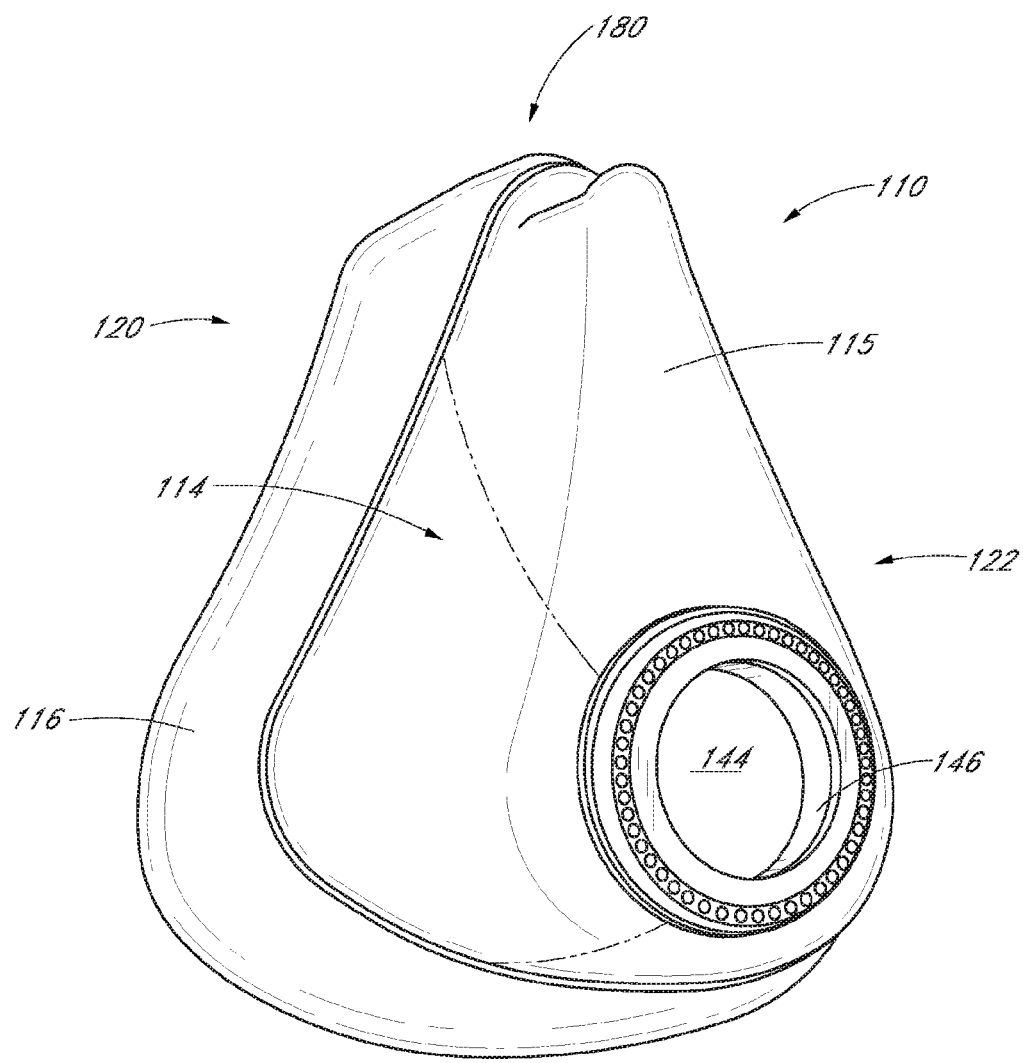
FIG. 5 is a front perspective view of a seal chamber.
Figure 6:
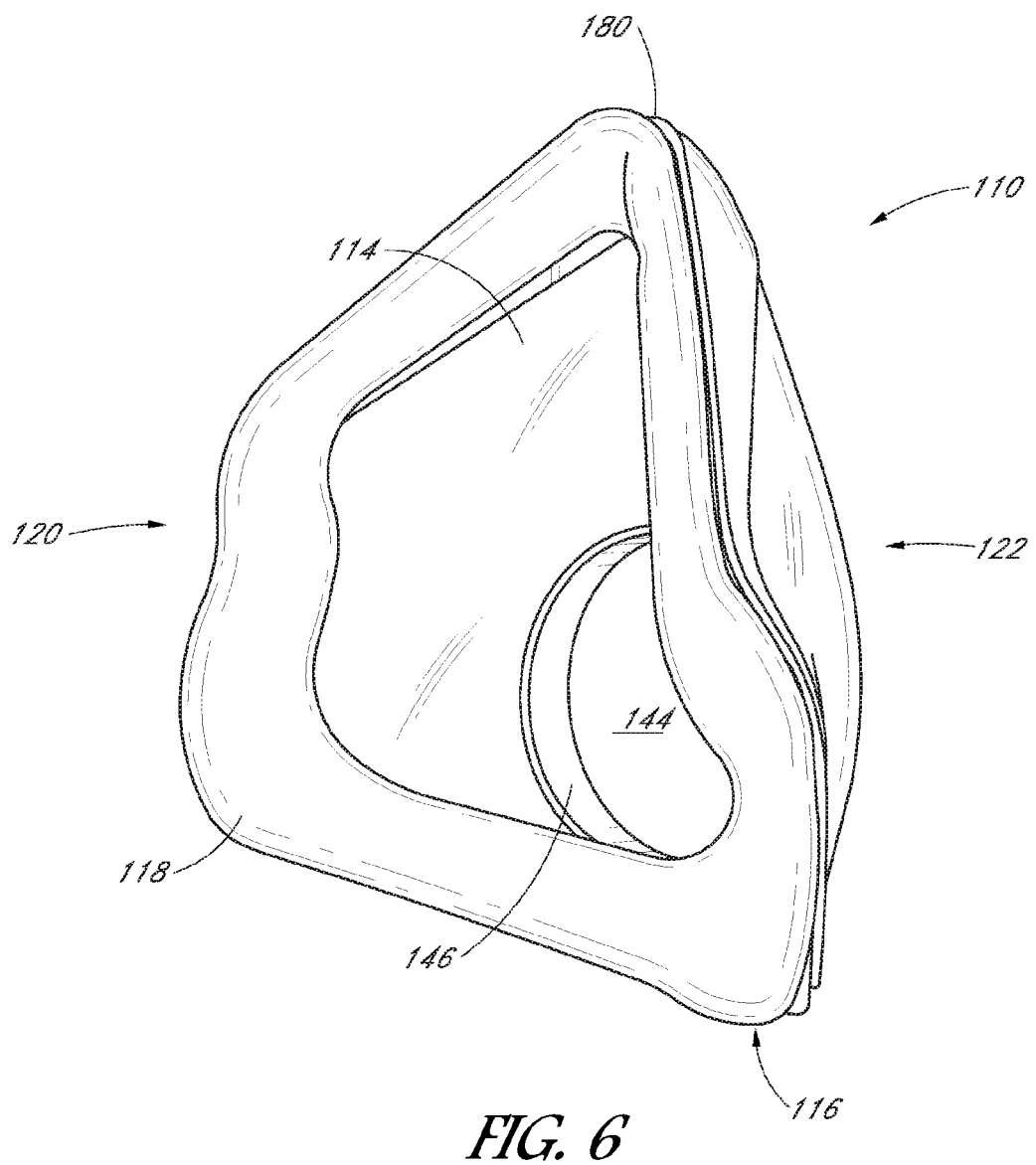
FIG. 6 is a rear perspective view of the seal chamber of FIG. 5.

As illustrated in FIGS. 5 and 6, the seal chamber 110 can comprise a mask base 114 and a mask seal 116 around the perimeter of the mask base 114. In some configurations, the mask base 114 and mask seal 116 can be integrated into a single component. For example, the mask seal 116 can be overmolded onto the mask base 114. Attempts to separate the mask seal 116 and the mask base 114 may result in the destruction of the seal chamber 110. In some configurations, the mask base 114 and mask seal 116 can be formed separately and secured together, such as through adhesives, welding, or thermal bonding.

In some configurations, the mask base 114 and the mask seal 116 are removably connected. For example, the mask base 114 can snap together with the mask seal 116. In another example, the mask base 114 and mask seal 116 can have complementary structures that connect together, such as a tongue and groove attachment. The illustrated configuration advantageously has a construction that is easy to clean and service.

The mask base 114 can be relatively more rigid, stiffer or more inflexible than the mask seal 116. In some configurations, the mask base 114 is formed of a polycarbonate material. In some configurations, at least a portion of the mask base 114 is formed of a polycarbonate or other rigid or semi-rigid material. In some configurations, the mask base 114 is formed at least partially of silicone or another suitable material. The silicone portion of the mask base 114 can be formed to be relatively thicker compared to the more flexible portions of the mask seal 116. The mask base 114 can provide at least some structural support to the mask seal 116 in the illustrated configuration.

With continued reference to FIGS. 5 and 6, the illustrated seal chamber 110 comprises a generally cup-shaped configuration. A proximal end 120 defines an open end of the illustrated seal chamber 110 while a distal end 122 defines a generally closed end of the seal chamber 110. The mask seal 116 extends laterally outward from the mask base 114 as shown in FIG. 6. In the illustrated configuration, the mask seal 116 is generally triangular shaped when viewed from the back and configured to fit over the user's mouth and nose. The upper portion of the seal chamber 110 comprises an apex 180. The apex 180 can be defined as a tip, a top and an angular summit of the mask seal 116, which apex 180 is positioned in proximity to the nose of the user when in use. The side walls of the mask seal 116 converge at the apex 180 in the illustrated configuration.

Figure 7:
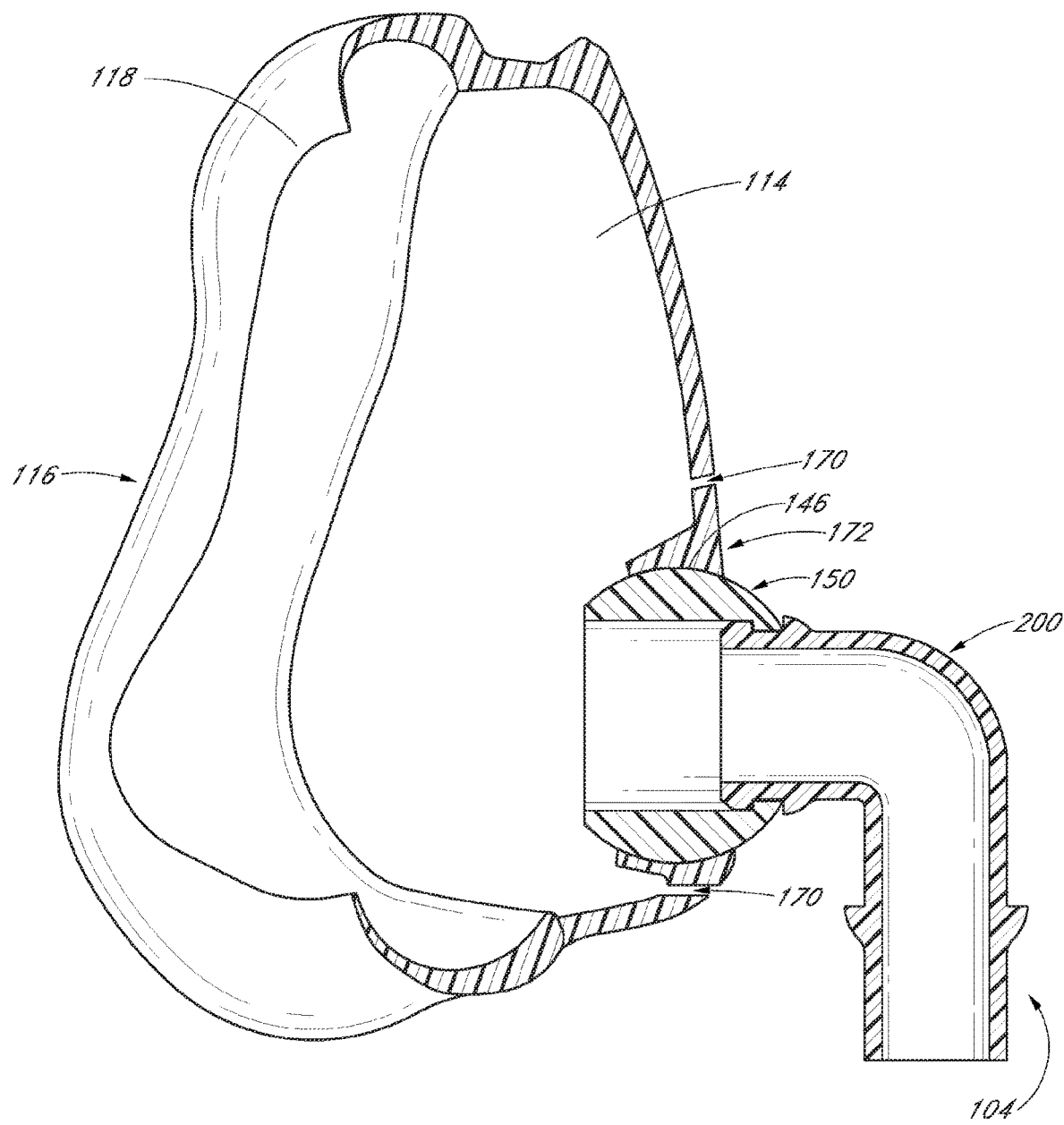
FIG. 7 is a cross-sectional view of a seal chamber and connection port assembly.

As illustrated in FIG. 7, the mask seal 116 can have a pliable edge that curls rearward and inward and has an abutment surface 118 that lies against the user's face, in situ, to form a seal or semi-seal around the user's mouth and nose. The abutment surface 118 is configured to underlie a lower lip of the user, extend along the outside of the mouth, extend upward along the cheekbones and extend across the bridge of the nose of the user. The illustrated abutment surface 118 defines a generally tear-drop shaped opening. When the mask assembly 102 is seated on the face of the user, the abutment surface 118 can lie flat over the bridge of the nose, the cheekbones, the outside of the mouth and below the lower lip of the user. With a supply of positive pressure air, the mask seal 116 is configured to balloon and seal or substantially seal against the face of the user to reduce or eliminate the likelihood of leakage between the abutment surface 118 and the face of the user.

In other embodiments, the mask seal can have any functional sealing configuration, such as an abutment surface in combination with an accordion-like suspension to help conform to the user's facial anatomy. In another example, the mask seal can include overlapping or rolling portions, such as described in International Patent Application Publication No. WO 2012/140514, which is hereby incorporated by reference, in its entirety.

In the configuration illustrated in FIGS. 5 and 6, the seal chamber 110 has an upraised portion 115 configured to accommodate the nose of the user. The upraised portion 115 allows the mask base 114 to fit over the user's nose while minimizing the amount of dead space in the seal chamber 110, which can advantageously limit the amount of exhaled gases that are rebreathed by the user.

With continued reference to FIGS. 5 and 6, the seal chamber 110 also comprises a passage 144 disposed generally in the central portion of the mask base 114. The passage 144 is defined by a passage wall 146 that generally surrounds the passage 144. The passage wall 146 can be generally tubular and extend through the wall of the mask base 114.

Figure 8:
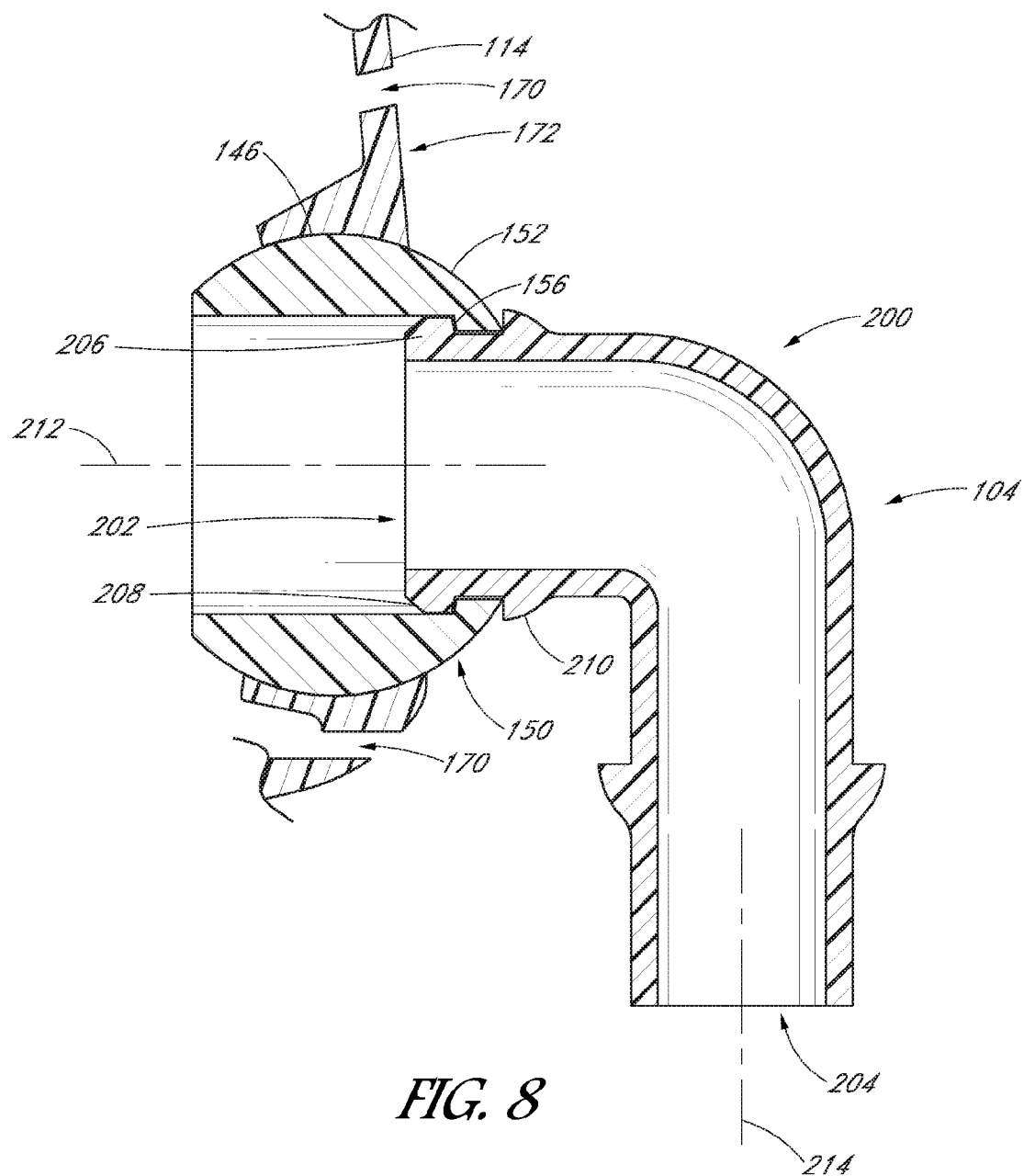
FIG. 8 is a close-up of the cross-sectional view of FIG. 7 showing a ball joint.

As illustrated in the cross-sectional view of FIGS. 7 and 8, the passage wall 146 can be a ball socket with a concave surface configuration such that the passage 144 can receive a ball end 150 of a connection port assembly 104. The ball end 150 has an outer surface 152 that is contoured to be snap fit into the passage wall 146 of the seal chamber. The ball joint between the passage 144 and ball end 150 can allow the surfaces to slide relatively freely with each other such that the angle between the connection port assembly 104 and seal chamber 110 can be easily changed. In some configurations, the connection port assembly 104 and seal chamber 110 can be configured for rotation or swiveling without having a ball joint configuration, such as with hinges or flexible bushings. In another example, the connection port assembly and the seal chamber can be connected together with a bellows structure (i.e., accordion-like structure).

Figure 9:
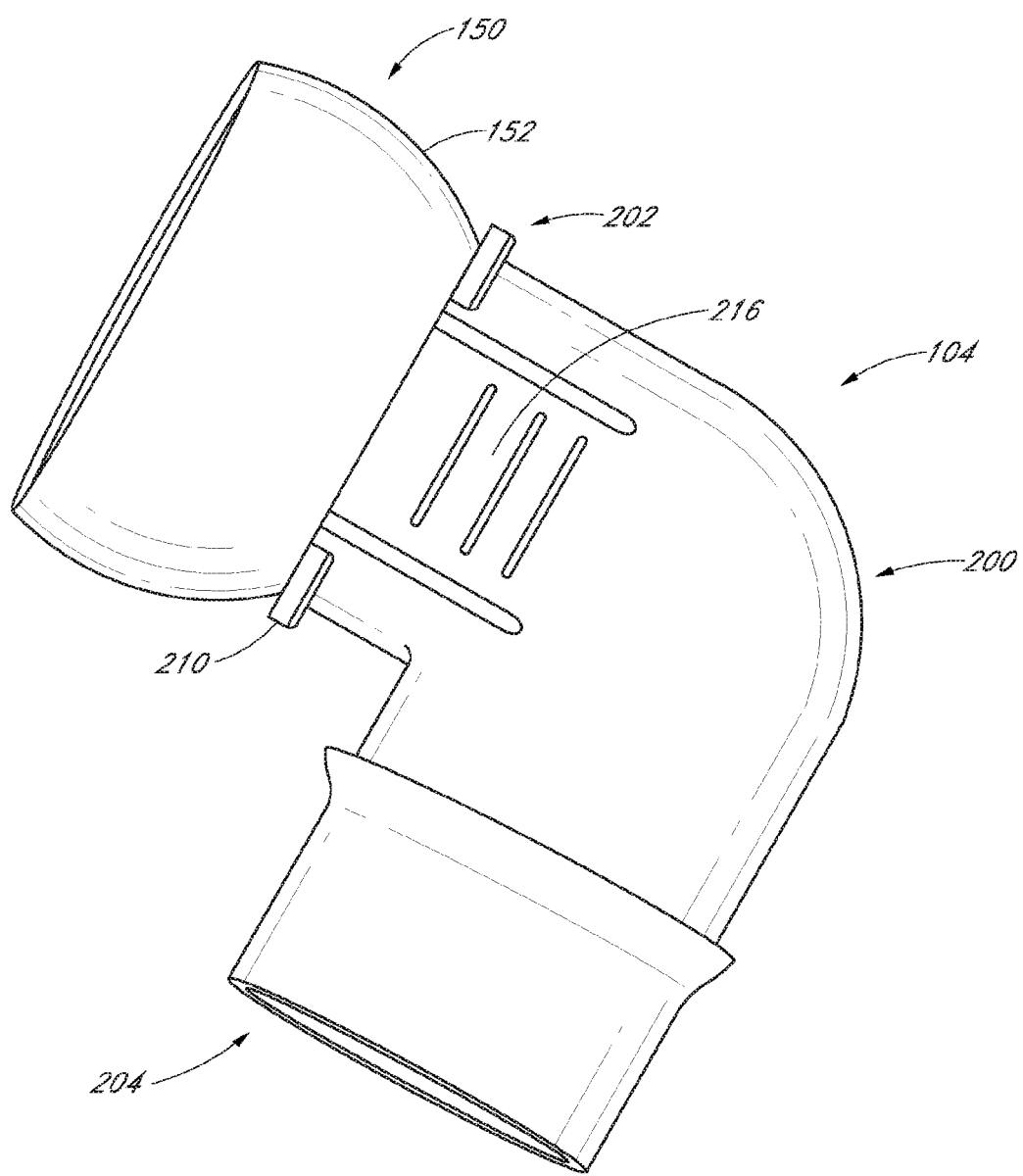
FIG. 9 is a perspective view of a connection port assembly.

With reference to FIG. 9, the connection port assembly 104 can include a fluid connector 200 and a ball end 150. The fluid connector 200 has a channel extending from a first end 202 to a second end 204. The first end 202 has a longitudinal first axis 212 and the second end 204 has a longitudinal second axis 214. In the illustrated embodiment, the fluid connector 200 is an elbow with about a 90 degree angle between the first axis 212 and second axis 214. In some embodiments, the fluid connector can have a bend of any suitable angle ranging from at least approximately 30 degrees and/or less than or equal to approximately 150 degrees, such as about 120, 135 or 150 degrees. In other embodiments, the fluid connector can be a straight tube without a bend.

The first end 202 can be configured to couple with the ball end 150 and the second end 204 can be configured to connect to a conduit that is in fluid communication with a respiratory gases supply. The first end 202 and ball end 150 can be releasably connected, preferably with a quick release connection. The ball end 150 is configured to couple to the passage 144 of the mask base 114 to provide a ball joint, as illustrated in FIG. 8. The ball joint provides the connection port assembly 104 with freedom of motion to accommodate forces exerted by the connected gases supply conduit. The ball joint provides improved wearer mobility and reduces hose drag, which may lead to displacement of the mask and undesirable leaks in the interface during use. The connection port assembly 104 can rotate and have angular movement relative to the passage 144 to improve user comfort and limit stresses exerted on the interface. For example, as the user moves his/her head, the ball joint can help prevent the gases supply conduit from pulling on the interface and disturbing the fit of the mask assembly on the user's face.

Figure 8A:
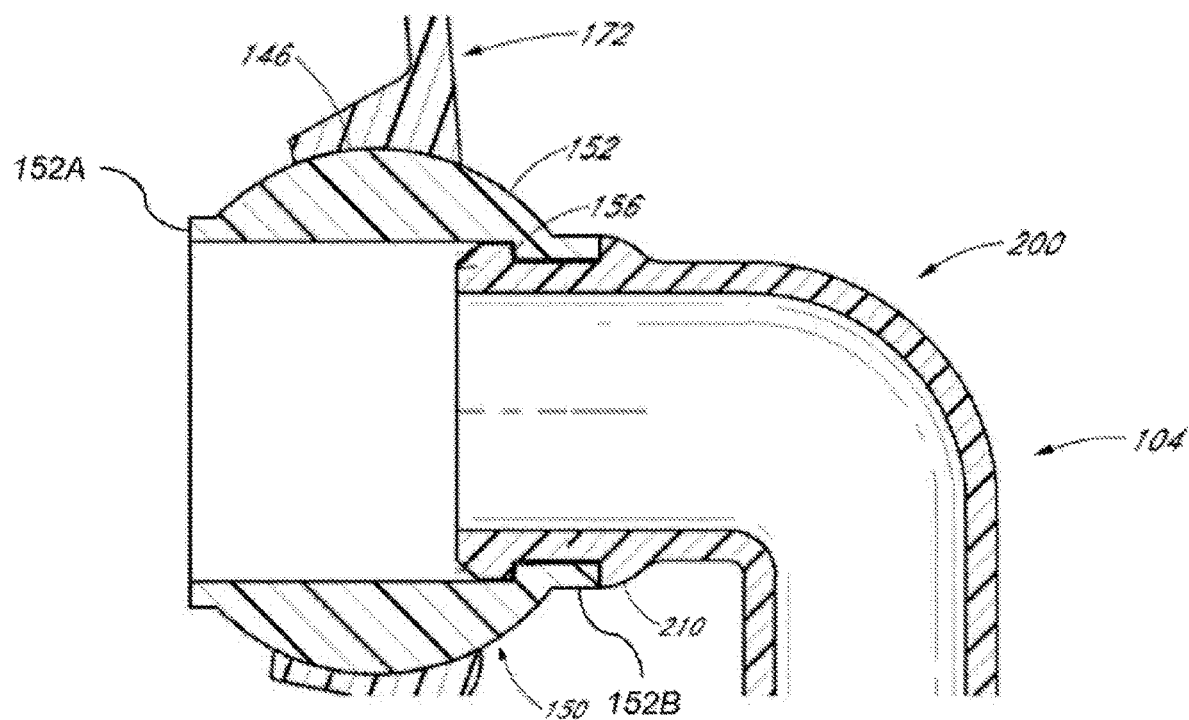
FIG. 8A is a close-up cross-sectional view similar to that of FIG. 8 of an alternative embodiment ball joint.
Figure 10:
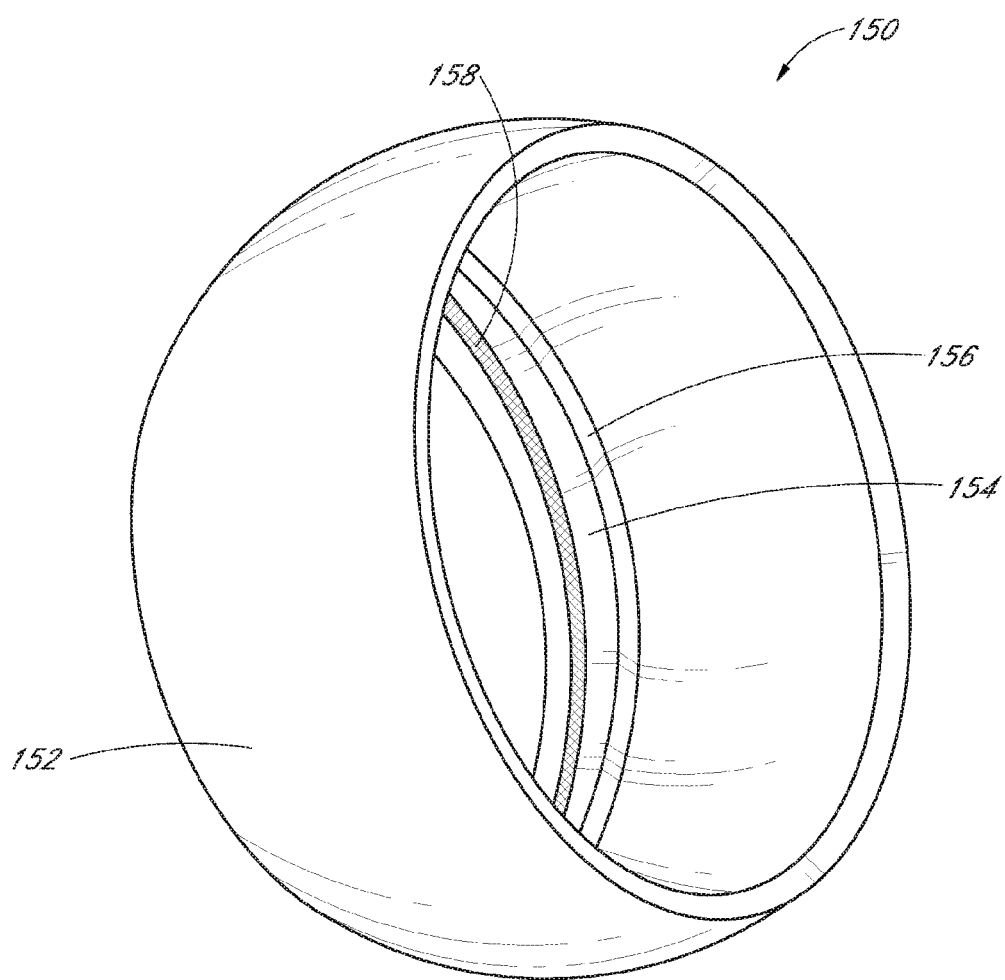
FIG. 10 is a perspective view of a ball end.
Figure 11:
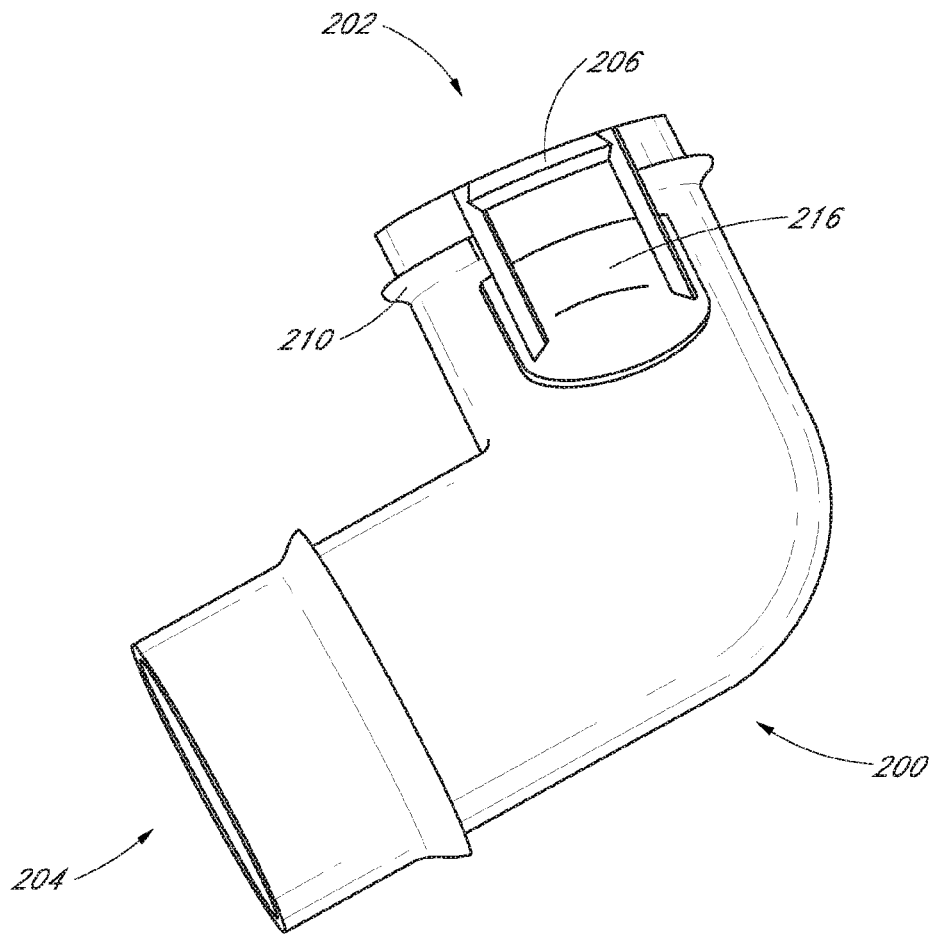
FIG. 11 is a perspective view of a fluid connector.

With reference to FIG. 11, the first end 202 can have a functional coupler to releasably connect to the ball end 150. In the illustrated embodiment, the first end 202 includes a protrusion 206 toward the opening of the first end 202. The protrusion 206 can have a chamfered edge 208 so that it can be easily inserted into the ball end 150. With reference to FIG. 10, the ball end 150 can have an inner flange 154 with a shoulder 156, or a groove that engages with the protrusion 206. As illustrated in FIG. 8, once the fluid connector 200 is inserted into the ball end 150, the protrusion 206 engages the shoulder 156 to hold the fluid connector 200 and ball end 150 together. The fluid connector 200 can also have a stop 210 to limit how far the fluid connector 200 can be inserted into the ball end 150. The fluid connector 200 is limited in movement along the longitudinal first axis 212 by the protrusion 206 on one side and the stop 210 on the other side, but the fluid connector 200 can rotate about the first axis 212. The inner flange 154 and the first end 202 can be coaxially located, allowing the fluid connector 200 to rotate 360 degrees relative to the ball end 150. FIG. 8A is a close-up cross-sectional view of an embodiment which is similar to that of FIG. 8, and in FIG. 8A the same reference numerals as in FIG. 8 indicate the same parts, except that in the embodiment of FIG. 8A structures are provided at the ball end 150 on the front side of the ball and at the ball end 152 at the rear or patient side of the ball which limit the extent of movement of the ball within the passage 144 of the ball socket. The ball rotation limiting structure or structures may prevent the ball socket from rotating within the air vent module 172 or seal chamber (or mask frame in another embodiment) when the fluid connector 200 is not inserted into the ball socket, to an extent that the entrance to the passage 144 in the ball socket is obscured in part or whole by the air vent module or seal chamber so that it is not possible to insert the fluid connector into the passage 144 of the ball socket. In the embodiment shown in FIG. 8A an annular ring 152B is provided around the entrance to passage 144 on the front side of the ball, and a similar annular ring 152A is provided around the exit to passage 144 at the rear or patient side of the ball, to so limit rotation of the ball socket within the air vent module 172 or seal chamber. Alternatively only ring 152A around the exit to passage 144 at the rear or patient side of the ball, or only ring 152B around the entry to passage 144 at the front side of the ball may be provided. Alternatively again ball rotation limiting structure or structures may comprise one or more protrusions at or around the entry or exit to passage 144 at the front or rear side of the ball, or any other structure associated with the ball socket and/or air vent module or seal chamber (or mask frame in another embodiment) which prevent the ball socket from rotating when the fluid connector 200 is not inserted into the ball socket to an extent that the entrance to the passage 144 in the ball socket is obscured preventing insertion or re-insertion of the fluid connector.

In some embodiments, the connection between the fluid connector 200 and ball end 150 can have a sealing flap 158 as illustrated in FIG. 10. The sealing flap can be a pliable material that protrudes from the inner circumference of the ball end 150 or from the outer circumference of the fluid connector 200 to help form a seal between the fluid connector 200 and ball end 150. The sealing flap 158 can be integral with the fluid connector 200 or integral with the ball end 150. For example, the sealing flap can be overmoulded to the ball end 150 or fluid connector 200. In some configurations, the sealing flap can be a separate piece, such as an o-ring, that is adhered or otherwise attached to the ball end 150 or fluid connector 200. The sealing flap can help seal the joint between the fluid connector 200 and the ball end 150 to help reduce fluid leaks and associated noise of fluid leaks. In embodiments without a ball joint, the sealing flap can be disposed between the fluid connector and seal chamber.

The fluid connector 200 can have a release button 216 to enable quick release of the fluid connector 200 from the ball end 150. In the embodiment illustrated in FIG. 11, there are two release buttons 216 on either side of the fluid connector that are attached to the protrusion 206. The release buttons 216 can be squeezed to displace the protrusions 206 from engagement with the inner flange 154. With the protrusions 206 released from the inner flange 154, the fluid connector 200 can be disconnected from the ball end 150. In some embodiments, the release button 216 can have other known functional coupler designs.

The release button 216 can at least partially be made of an elastic material to allow elastic deformation. For example, the release buttons 216 can be a thermoplastic elastomer that is overmoulded onto the fluid connector 200. The release buttons 216 advantageously allow the fluid connector 200 to be released from the mask frame 112 quickly and easily, whilst the mask is being worn. This can allow users to temporarily disconnect from the gases source without removing the mask, such as when getting up in the night to use the restroom. An easily removable fluid connector 200 can also beneficially help easy cleaning and servicing of the mask assembly.

The combination of the ball joint and releasable fluid connector 200 advantageously improves ease of use, comfort and the efficacy of treatment. As explained above, the ball joint improves flexibility and comfort of the interface. For example, the ball joint can rotate and swivel to help isolate patient movement and minimize transfer of forces to the conduit, which can reduce hose drag and provide improved freedom of movement for the patient, especially during sleep. Also, the quick releasable feature of the fluid connector helps make the interface easier and more comfortable to use. These features help and encourage the user to use the treatment, improving its efficacy. The combination of other features also contributes to the improvements of the disclosed device, such as the overmoulded release button 216, ball joint located in seal chamber 110 rather than the mask frame 112 and the silicone sealing flap between the fluid connector 200 and ball end 150. Having the connection port assembly 104 connected to the seal chamber 110 may also help minimize bulk and weight and may help to move the centre of gravity of the mask assembly closer to the users face, which can improve mask stability.

The second end 204 can be configured for connection to a conduit that is in fluid communication with a respiratory gases supply. The second end 204 can be sized for connection to standard sized conduits used in the industry. In some embodiments, the second end 204 can have a swivel connection to provide freedom of movement between the interface and gases supply conduit. For example, the second end can comprise a generally cylindrical inner component and a generally cylindrical outer component that slides over the inner component to provide rotational movement of the outer component. Some configurations of a swivel connection are described in International Patent Application Publication No. WO 2012/140514, which is hereby incorporated by reference, in its entirety.

While not shown, the fluid connector can comprise one or more bias flow vent holes. The bias flow vent holes preferably are positioned in a forwardly directed orientation such that any bias flow does not directly impinge upon the user.

With reference to FIG. 3, the mask assembly 102 can have bias flow air vents 170 for expelling exhaled air. In the illustrated embodiment, the air vents 170 comprise a plurality of through holes arranged in an annular configuration around the passage 144. The radial diffusion of exhaust air helps reduce air drafts that may disturb the user or their bed partner and minimises noise levels. Generally, relatively smaller hole sizes produce less airflow noises compared to a larger hole size given the same flow velocity through both hole sizes. The plurality of holes helps reduce airflow noises compared to one or a few holes having the same vent area when expelling a given volume of exhaust air. The location of the air vents 170 around the passage 144 is aesthetically pleasing and may be beneficial in terms of manufacturability, as explained below.

Figure 12:
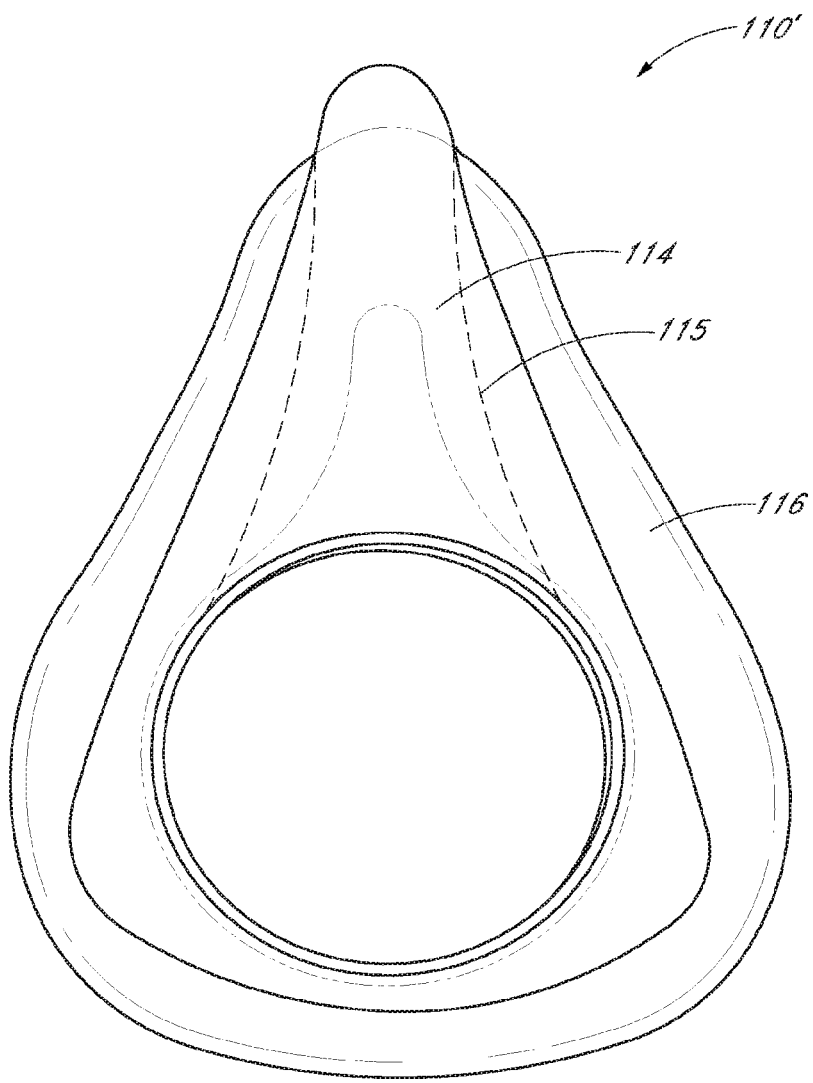
FIG. 12 is a front elevational view of a mask base.
Figure 13:
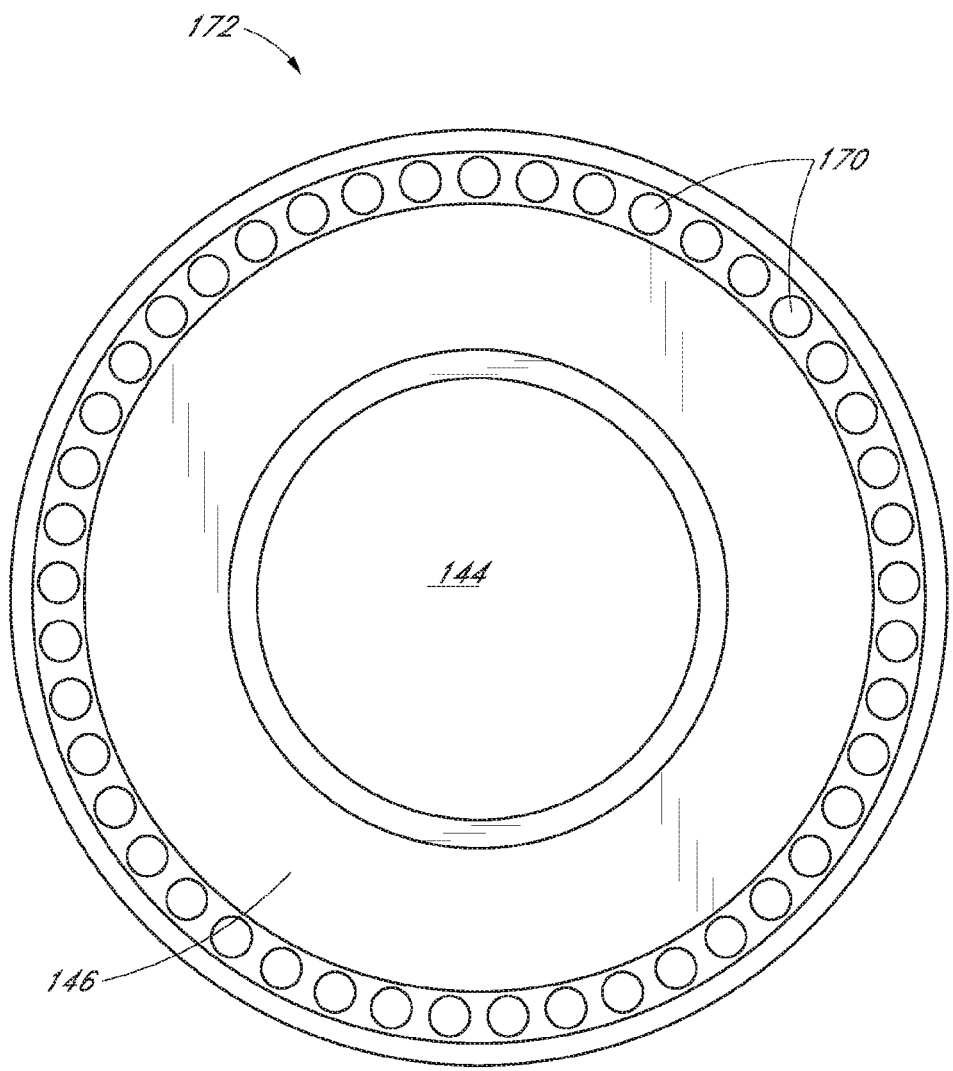
FIG. 13 is a front elevational view of an air vent module.

In some embodiments, the bias flow air vents 170 can be formed as a separate component from the seal chamber or mask frame. The air vent module 172 can be an annular component with air vent holes arranged in an annular configuration, as illustrated in FIG. 13. The air vent module 172 can be permanently or temporarily assembled to the seal chamber or mask frame. FIG. 12 illustrates a seal chamber 110' that is configured to couple with the air vent module 172. For example, the air vent module can have threads that mate with complementary threads on the seal chamber. In other configurations, the air vent module can have any type of functional coupler to mate the air vent module to the seal chamber. In these configurations, the air vent module can be removed easily for service, cleaning or replacement.

In some configurations having a separate component, the air vent module 172 can include the passage 144 with ball socket such that the air vent module 172 is attached to the seal chamber 110' and the connection port assembly 104 is attached to the air vent module 172. In other configurations, the passage 144 can be a part of the seal chamber such that the connection port assembly is attached to the seal chamber and the air vent module is attached to the seal chamber and disposed around the passage 144.

In configurations with a permanently attached air vent module, the air vent module can be overmoulded to the seal chamber for a permanent attachment. The overmoulding can include a flexible gusset between the air vent module and the seal chamber that helps with flexibility. In other configurations, the air vent module can be permanently attached using, for example, adhesives or ultrasonic welding.

The separate air vent module advantageously allows improved manufacturing and product quality. By having the vents in a separate component the moulding of the small and detailed vent apertures can be better controlled. By moulding the vents as a separate component, the part tolerances can be better controlled and result in more consistent hole dimensions having a more consistent flow rate performance between parts. Moulding a separate vent module may allow for production of more complex vent designs as a result of not having to accommodate undercuts and other geometric restrictions of other components, such as the seal chamber for example. Improved control of the part dimensions may also improve control of noise levels, such as by controlling the part contours to produce a smooth air flow through the holes.

Figure 17:
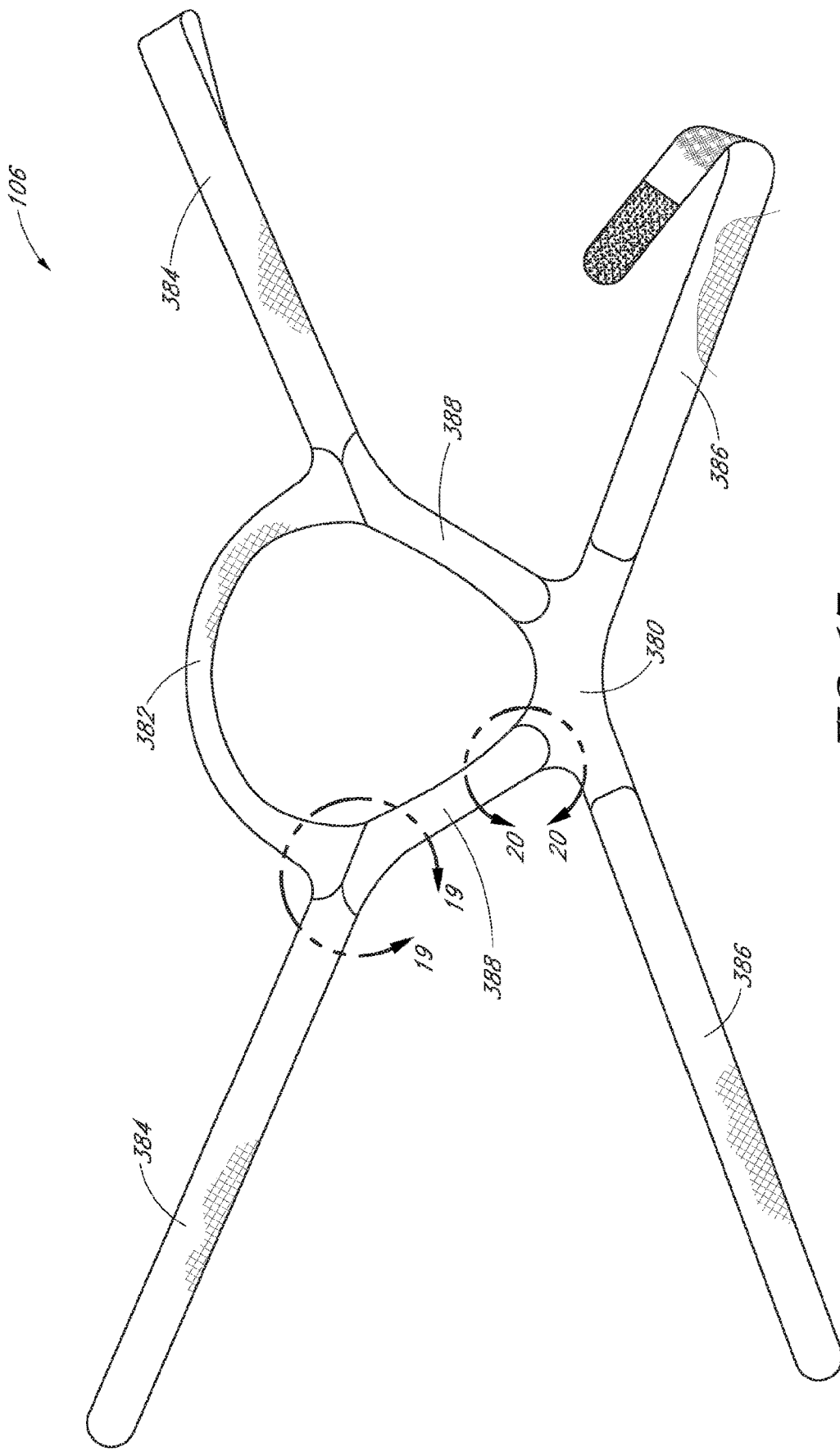
FIG. 17 is a plan view of a headgear assembly.
Figure 18:
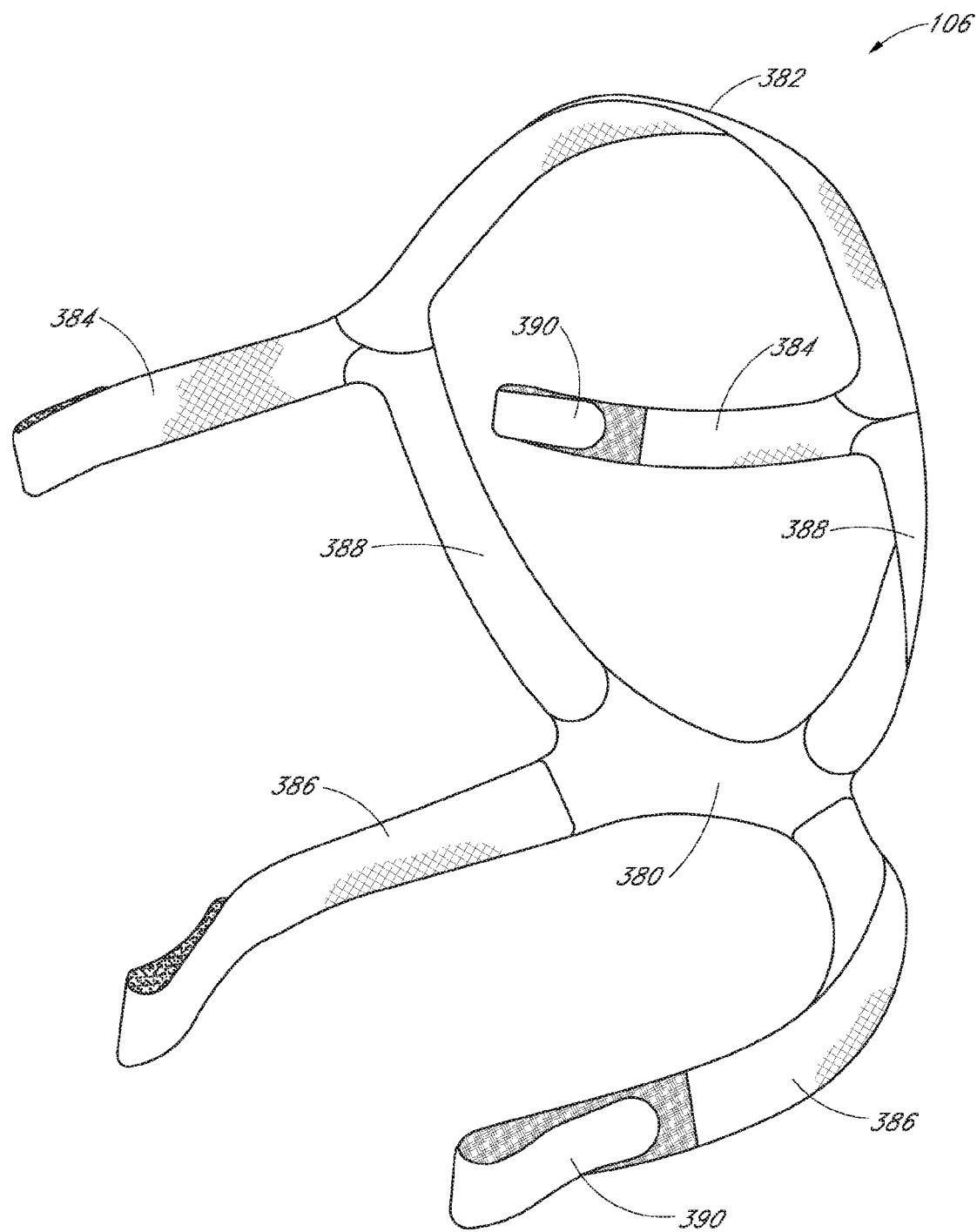
FIG. 18 is a perspective view of a headgear assembly.

With reference to FIGS. 2, 17 and 18, the headgear assembly 106 can comprise a back strap 380, a top strap 382, upper side straps 384 and lower side straps 386 and upper arms 388. In use, the back strap 380 extends around the back of the head of the user U at a location generally above a nape of the neck but generally below the occipital protuberance. At a location rearward of the ear of the user, the back strap 380 can fork into an upright strap 388 and the lower side strap 386. In the illustrated embodiment, the upright strap 388 extends upward to a location above the ear of the user. The lower side strap 386 extends generally below the ear of the user and extends slightly forward of the ear to the mask assembly 102. Other embodiments of headgear assemblies also can be used, such as those described in International Patent Application Publication No. WO 2012/140514, which is hereby incorporated by reference, in its entirety.

In the illustrated configuration, the back strap 380 is connected to the upright strap 388 and the lower side strap 386. The upright strap 388 is also connected to the upper side strap 384 and top strap 382. The straps can be connected together in any suitable manner, such as stitching or ultrasonic welding, as described below.

Figure 14:
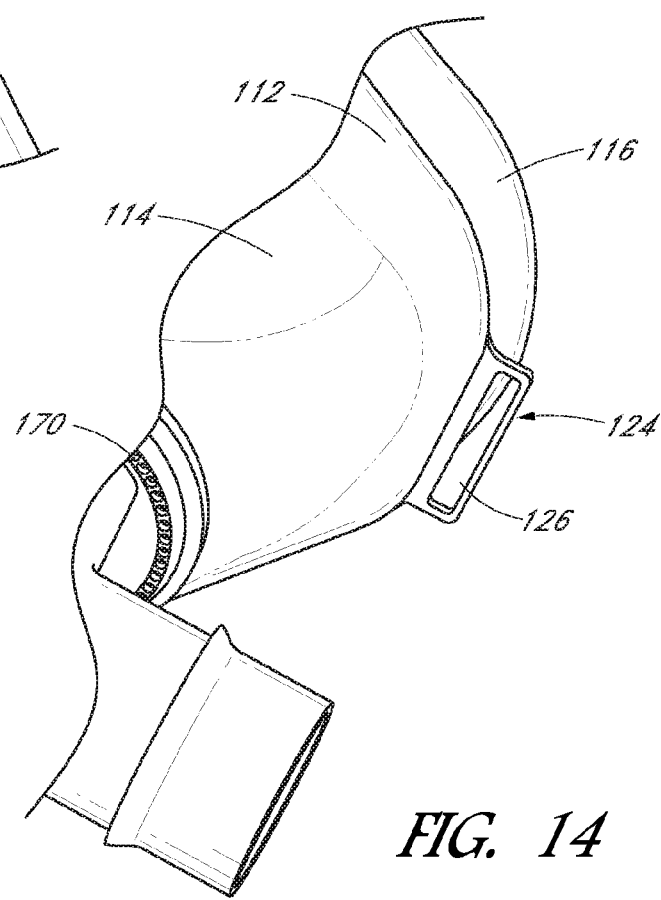
FIG. 14 is a close-up perspective view of a mask assembly showing a headgear attachment.

The headgear assembly 106 can be attached to headgear attachments 124, 136 on the mask assembly 102, as illustrated in FIG. 2. With reference to FIG. 14, the mask frame 112 can have two first headgear attachments 124 toward the bottom of the frame that are configured to fasten with the lower side straps 386. Similarly, with reference to FIG. 15, the forehead rest 132 can comprise two second headgear attachments 136 that are configured to fasten with the upper side straps 384.

The first headgear attachments 124 can have first slots 126 for attaching the lower side straps 386 and the second headgear attachments 136 can have second slots 138 for attaching the upper side straps 384. The side straps can be inserted through the slots and looped back onto themselves. An adjustment mechanism 390, such as Velcro® tabs, buttons, buckles, clips or similar releasable fastener, can be disposed on the side straps for securing the adjustable loops. The adjustment mechanism 390 can allow for adjustment of the force between the mask seal 116 and the face of the user U. In the illustrated embodiment, the adjustment mechanisms 390 are located forward of the ear. The positioning of the adjustment mechanisms 390 can help the user to adjust the side straps 384, 386 without much difficulty. Other suitable adjustment mechanisms can be used.

In some configurations, the adjustment mechanism 390 can include ends with an embedded panel having hook fasteners or the like. The panels can be located on the ends such that the ends can be secured to another portion of the corresponding side strap when the side strap is folded back over itself. For example, the embedded panels can be comprised of a hook fabric and another portion of the corresponding side strap can have loop fabric (e.g., Velcro®). The ends with the hook materials can be fastened onto another portion of the corresponding side strap having the loop material, to secure the headgear assembly 106 to the mask assembly 102. In some configurations, the side strap can be made of the loop material such that the ends with the hook material can be coupled to any position along the length of the side strap. In other configurations, portions of the side strap can have the loop material and the ends can be coupled to the positions having the loop material portions. For example, panels with the loop material can be attached to various selected positions along the side strap. The panels with the hooks or loops can be attached to the ends or other positions of the side straps in any suitable manner. In some configurations, the panels are attached to the end by ultrasonic welding. For example, the panels can be located in a desired location along the arm and then the ultrasonic welding process can effectively melt the two materials together.

With reference to FIG. 17, the back strap 380, top strap 382 and upright straps 388 can form a generally annular shape. The annular shape encircles the occipital protuberance, or upper rear portion, of the users head. The annular shape can have a three-dimensional shape, as illustrated in FIG. 18. In the illustrated embodiment, the top strap 382 is curved and angled to better match the shape of the user's head when worn. The back strap 380 and upright straps 388 can also be curved and angled to better match the shape of the user's head. The three-dimensional shape advantageously improves ease of use in relation to fitting the mask and headgear assemblies. Comfort may also be enhanced by the three-dimensional shape as the headgear assembly can conform to the contours of the users head.

Preferably, the top strap 382 connects to the upper side straps 384 at a location generally above the ears of the user. In some embodiments, the top strap can be adjustable in length. For example, the top strap can comprise two pieces that can attach together at variable lengths with functional adjustable couplers such as Velcro®, buttons, buckles, and the like.

The headgear assembly 106 can be formed of any suitable material. In some configurations, the headgear assembly 106 can be covered with or have at least some portion formed of a hook-fastener receptive breathable composite material. In some configurations, the flexible headgear assembly 106 can be at least partially formed of Nylon/Lycra Breath-O-Prene® material. In some embodiments, when a 150 mm long by 20 mm wide sample of the material is subjected to a 10 N axial load, the sample elongates to about 207 mm, which is an elongation of about 38% caused by the 10 N axial load. Thus, the material preferably can be fairly elastic. In some embodiments, the headgear assembly 106 can comprise one or more rounded edges. The rounded edges can be formed in any suitable manner. In some configurations, the rounded edges are formed by applying heat and pressure to the edges of the headgear assembly 106. In some configurations, the rounded edges are formed in a manner similar to the techniques described in U.S. Pat. No. 3,295,529, which is hereby incorporated by reference in its entirety.

In some configurations, ultrasonic welding can be used to join components of the headgear assembly. The headgear assembly can be made of a material that is amenable to ultrasonic welding, such as Breath-O-Prene®. Ultrasonic welding may advantageously enhance comfort, fit and/or performance of the headgear assembly. Ultrasonic welding of the headgear components is also useful in reducing costs as there is less material wastage than is associated with headgear that is cut as a single piece.

Components may be joined along their length or may be stacked and ultrasonically welded one on top of the other. Ultrasonic welding can be accomplished with a sonotrode that produces ultrasonic vibration. The vibration of the sonotrode creates energy which is converted into heat energy by an anvil, welding the components together.

Ultrasonic welding can be used to produce a flush joint with generally the same thickness as the surrounding material. When stitching two components together, the components are usually overlapped to produce a strong stitch, and hence the final thickness of the stitched portion is the thickness of the two components added together. Unlike stitching, ultrasonically welded components may be overlapped and then welded, which results in a melted portion at the point contact between the components that are welded. The thickness of the joint may be no thicker than the thickness of the first or second component, or may be less than the thickness of both components combined.

An ultrasonically welded headgear assembly is illustrated in FIG. 17. As shown, ultrasonic welding can be used to join two or more components together. In the illustrated embodiment, three components (i.e., the top strap 382, upright strap 388 and upper side strap 384) are ultrasonically welded together. Also, the upright strap 388 is ultrasonically welded to the back strap 380. The lower side strap 386 is ultrasonically welded to the back strap 380.

Figure 19:
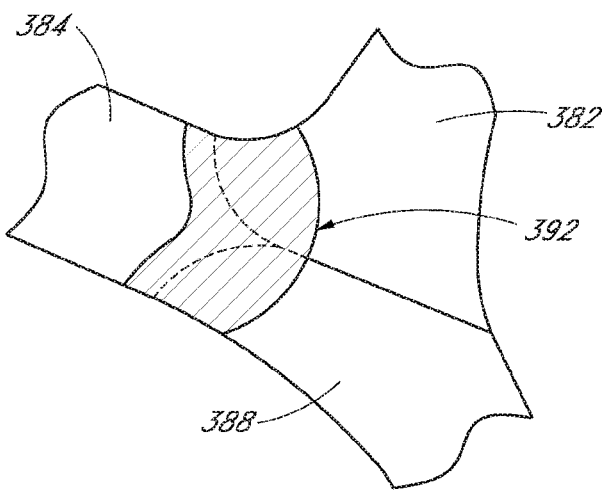
FIG. 19 is a close-up view of a joint between three straps.
Figure 20:
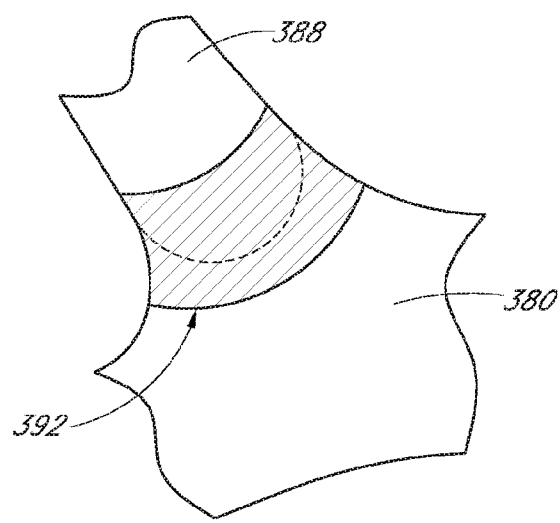
FIG. 20 is a close-up view of a joint between two straps.

FIG. 19 illustrates an enlarged detail from FIG. 17 showing the three components ultrasonically welded together. Portions of the top strap 382 and the upper side strap 384 overlap, and portions of the upright strap 388 and upper side strap 384 also overlap. These overlapping portions can be welded together, as shown by the welded region 392. The top strap 382 and upright strap 388 can also overlap and be welding together in some embodiments. These overlapping components can be placed in an ultrasonic welding tool for ultrasonic welding. The ultrasonic welding tool welds together overlapping portions by applying ultrasonic vibrations in order to join the overlapping components in a single process. Similarly, FIG. 20 illustrates the welded region 392 between the back strap 380 and the upright strap 388.

Figure 21:
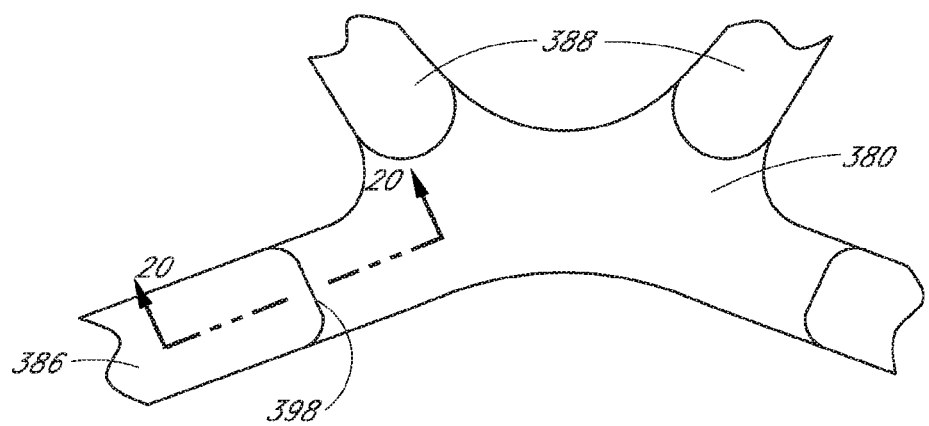
FIG. 21 is a close-up view of a portion of the headgear assembly of FIG. 17.
Figure 22:
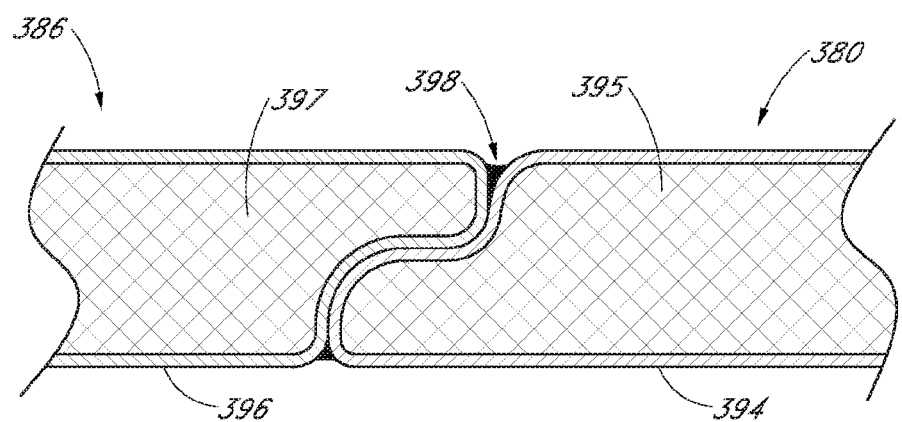
FIG. 22 is a cross-sectional view of a ultrasonic weld joint in FIG. 21.

FIG. 21 shows an ultrasonic weld joint 398 between the back strap 380 and lower side strap 386. FIG. 22 is a cross-sectional view of the ultrasonic weld joint 398. The back strap 380 can include an outer cover 394 and an inner component 395. The lower side strap 386 can similarly have an outer cover 396 and an inner component 397. The other straps can have similar constructions. The ultrasonic welding process can produce a joint 398 that interconnects the back strap 380 and the lower side strap 386. The outer covers 394, 396 can be aligned thereby providing a smooth, even joint which enhances patient comfort. In contrast, a stitched joint would result in the connected components being connected with a raised area of thread which provides an uneven, rough surface that may be uncomfortable to the user.

In some configurations, portions of the headgear assembly can be substantially non-stretchable. For example, the back strap 380, top strap 382 and upright straps 388 can be non-stretchable such that the portion that encircles the occipital region of the users head is made from non-stretch material. In some configurations, the top strap can be adjustable in length, as discussed above. Some benefits of having a non-stretch headgear portion that encircles the rear (occipital) region of the users head may include helping to prevent over-tightening of the headgear and helping to better support the weight of the headgear assembly to limit the slipping of the mask assembly down over the users head during use. These benefits can result in improved user comfort and efficacy.

By resisting elongation of at least a portion of the headgear assembly, the non-stretchable portions can help maintain the headgear assembly in a desired shape and help maintain the headgear assembly at a desired location relative to a back of the user's head. Without the use of non-stretchable portions around the back of the user's head, elongation in the back of headgear assembly may, for example, cause the headgear assembly to elongate and move downward toward the user's neck and/or diagonally towards the user's chin when increasing loads are applied to the lower side straps.

If the portions of the headgear assembly around the occipital protuberance were stretchable, then when increasing loads are applied to the headgear assembly, the elastic nature of the back strap 380, top strap 382 and upright straps 388 would allow the headgear assembly to elongate and deform. The deformation may allow the back strap 380 to move downward along the neck of the user. With downward movement, more force from the back strap 380 would undesirably be applied to the neck rather than the head. Because the headgear assembly may be worn for a period of minutes to hours, or for a period of hours to days when used for respiratory therapy, the lowered positioning of the back strap 380 can create discomfort for the user. In some situations, particularly when the top strap is stretchable, the mask assembly may stretch and pull the headgear assembly generally in the direction of the user's chin. This can cause a pinching sensation on the occipital region of the user's head as the stretchable headgear assembly tries to rebound to its original shape. The pinching can apply pressure to the scalp, which creates discomfort for the user.

In some configurations, the non-stretchable portions can comprise of a substantially non-stretch insert. The non-stretch insert can be attached to the headgear assembly, for example, by over-lock stitching, by ultrasonic welding, by use of glue or other adhesives, or by any other method known to those of skill in the art. When the non-stretch insert is attached to the headgear assembly, it can provide greater tension resistance, which allows the headgear assembly to support greater forces. Thus, the non-stretch insert can advantageously reduce deformation of the headgear assembly and aid in keeping it located in a desired position relative to the head and neck of the user.

In some configurations, one or more of the side straps 384, 386 can also be formed of a substantially inelastic or non-stretchable material. The side straps can be formed of a semi-rigid, self-supporting material such that the semi-rigid headgear assembly can assume a substantially three-dimensional shape and generally does not tangle. In some configurations, the semi-rigid strap does not stretch more than approximately 6 mm under a 30 N tensile load. In some configurations, the semi-rigid strap 482 does not stretch more than approximately 3 mm under a 30 N tensile load.

The non-stretchable characteristic can be achieved by embedding at least one relatively inelastic panel in the portion of the headgear assembly 106 that is desirably non-stretchable. The panel can be formed of a relatively low-stretch material, such as a polyester Breath-O-Prene® material, for example but without limitation. In some embodiments, when a 150 mm long by 20 mm wide sample of the material is subjected to a 10 N axial load, the sample elongates to about 160 mm, which is an elongation of about 7% caused by the 10 N axial load. Thus, the material preferably is fairly inelastic or non-stretch when compared to the more elastic material of the flexible portion.

In some configurations, the headgear assembly 106 can be semi-rigid to secure the mask assembly 102 to the user's head. Preferably, the top strap 382 and the upright straps 388 are more rigid than the other straps such that the headgear assembly 106 maintains its general shape as the headgear assembly 106 is being donned. In some configurations, each of the top strap 382 and the upright straps 388 supports its own weight. In some configurations, each of the top strap 382 and the upright straps 388 is structured to be tangle-free during donning. For example, the top strap 382 and the upright straps 388 have sufficient torsion stiffness to reduce the likelihood of twisting when being put on.

The semi-rigid headgear can be formed as a composite structure comprising a semi-rigid strap that is joined to a soft edging. For example, the soft edging can be bonded to the semi-rigid strap by plastic overmolding or by use of an adhesive. The soft edging can be butt joined to the semi-rigid strap, without the soft edging overlapping the semi-rigid strap, to maintain the continuous profile of the semi-rigid headgear. The semi-rigid strap can define and maintain the semi-rigid headgear shape as tension is applied from the straps to pull the mask assembly assembly 102 towards the user's head. In other words, the semi-rigid strap can be sufficiently rigid along its planar axis to prevent its upper and lower side straps 384, 386 from overly deforming under tension. The semi-rigid strap can be made from a variety of rigid or semi-rigid materials, including plastic or metal. In some configurations, the semi-rigid strap is made from PVC.

Especially in connection with a semi-rigid headgear assembly, it has been found that the shape holding, or self-supporting nature, can result in an overall assembly that is intuitive to fit. In particular, where the connection and/or headgear members are self-supporting such that they maintain a three-dimensional form as discussed earlier, the headgear can be fitted in the correct orientation with very little if any instruction. In a self-supporting arrangement, the tendency of the straps to not tangle also reduces the time taken to fit the overall assembly.

As used herein, the term "semi-rigid" is used to denote that the headgear assembly is sufficiently stiff such that the headgear assembly can assume a three-dimensional shape with dimensions approximating the head of the user for which the headgear is designed to fit while also being sufficiently flexible to generally conform to the anatomy of the user. For example, some of the other components (e.g., side straps) of the headgear assembly may also be partially or wholly "semi-rigid" such that the components are capable of holding a three-dimensional form that is substantially self-supporting. A "semi-rigid" headgear assembly is not intended to mean that each and every component of the headgear assembly is necessarily semi-rigid. For example, the substantially three-dimensional form that the self-supporting headgear assembly may assume may relate primarily to the rear and top portions of the headgear assembly. In addition, the semi-rigid headgear assembly may include semi-rigid regions that extend forward of the ears and above the ears when placed on the head of the patient.

The upper and lower side straps 384, 386 can be formed of a semi-rigid material, as well. Where used herein, the semi-rigid materials can include molded plastic or sheet materials that include, but are not limited to, homogeneous plastic materials and bonded non-woven fiber materials. In some configurations, the semi-rigid properties of the materials can be achieved with high-density foam material. The dense foam material can provide some structural rigidity to the upper and lower side straps, or other portions of the headgear assembly. In some configurations, the semi-rigid material can include textiles that are semi-rigid, such as denim or hemp.

In some configurations, the material can comprise a laminate structure of both conformable and semi-rigid portions, for example but without limitation. The semi-rigid straps may be of a self-supporting, resilient, substantially inelastic material, such as Santoprene, polyolefin, polypropylene, polyethylene, foamed polyolefin, nylon or non-woven polymer material for example but without limitation. In some configurations, the semi-rigid strap is formed from the polyethylene or polypropylene families. The material can be a low density polyethylene such as Dowlex 2517, which is a linear low density polyethylene that has a yield tensile strength of 9.65 MPa, a break tensile strength of 8.96 MPa, and a flexural modulus—2% secant of 234 MPa. The semi-rigid strap can be formed of a material such that the semi-rigid headgear is substantially shape-sustaining under its own weight regardless of its orientation.

In some configurations, the semi-rigid strap is formed from non-woven polyolefin (NWP), which is bonded (e.g., overmolded or laminated) with a polyolefin. In such configurations, the overmolded polyolefin material provides the principle shape sustaining properties. In addition, the softer NWP material is adapted to contact the skin and provide a desired comfort level. Furthermore, the NWP material may assist in providing the desired load bearing properties, such as the desired tensile load bearing properties.

A soft edging can cover or attach to at least a portion of the periphery of the semi-rigid strap. In some configurations, the soft edging does not cover the front or rear faces of the semi-rigid strap and is instead attached adjacent to the edge of the semi-rigid strap. For example, the thicknesses of the soft edging and semi-rigid strap can be the same at the location where they are joined together.

The soft edging can provide a soft, comfortable interface between the periphery of the semi-rigid strap and the user's skin. The soft edging can be made from a variety of soft materials, including but not limited to a plastic, an elastomer, silicone or thermoplastic polyurethane (TPU) plastic. The soft edging can have a Shore hardness in the range of 10-80 Shore A.

As used herein with respect to headgear and straps, "soft" is used to describe a hand of the material, which means the quality of the material assessed by the reaction obtained from the sense touch. In addition, as used herein with respect to headgear and straps, "conformable" is used to describe the ability of the material to conform to the anatomical features of the patient (e.g., around a facial feature). In particular, a strap including at least an element of "soft" and/or "conformable" material also may be "semi-rigid" and/or axially "non-stretchable."

The soft edging can have a uniform thickness, or in some configurations, an uneven thickness. For example, in some configurations the soft edging is the same thickness as the semi-rigid strap. In other configurations, the soft edging is thinner than the semi-rigid strap, forms a bulbous end to the semi-rigid strap, or is simply thicker than the semi-rigid strap. Any one particular soft edging thickness and shape can apply to a portion or the entire semi-rigid strap, or may be combined with any other particular covering thickness and shape.

Many other thickness configurations may be provided, as well. In addition, material thickness may be symmetrically or asymmetrically applied to the semi-rigid strap. For example, in some configurations the thickness of either end the soft edging is symmetrically applied to the semi-rigid strap. In some configurations the semi-rigid strap is selectively thickened to provide extra rigidity and support. Finally, in some configurations, venting through-holes are provided throughout the semi-rigid headgear (such as on the semi-rigid strap or on soft edging) to provide ventilation and sweat management.

Although certain embodiments, features, and examples have been described herein, it will be understood by those skilled in the art that many aspects of the methods and devices illustrated and described in the present disclosure may be differently combined and/or modified to form still further embodiments. For example, any one component of the face mask illustrated and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

What is claimed is:

1. A respiratory mask assembly, comprising:
   a seal chamber configured to cover at least a mouth or a nose of a user;
   an air vent module configured to engage with an opening of the seal chamber, the air vent module comprising:
   an annular component comprising a passage defined by a passage wall and forming a ball socket;
   a coupler configured to mate the annular component of the air vent module to the seal chamber of the respiratory mask assembly; and
   a plurality of vent holes arranged in a circular configuration to provide radial diffusion of exhaust air;
   a ball joint supported within the ball socket, the ball joint comprising:
   a first end;
   a second end;
   an outer spherical surface configured to rotatably engage the ball socket, the outer spherical surface extending from the first end to the second end; and
   an internal surface directly inside the outer spherical surface, wherein the internal surface comprises a shoulder; and
   a fluid connector that connects the respiratory mask assembly to a gases supply, the fluid connector comprising a releasable connection configured to couple to the first end of the ball joint, wherein the releasable connection comprises a protrusion on an outer surface of the fluid connector that is configured to engage the shoulder positioned at the internal surface of the ball joint.

2. The respiratory mask assembly of claim 1, further comprising a headgear assembly configured to secure the seal chamber to a head of the user.

3. The respiratory mask assembly of claim 2, wherein the headgear assembly comprises a back strap, a top strap and a pair of upright straps that cooperate to form an annular portion in use.

4. The respiratory mask assembly of claim 3, wherein the annular portion is non-stretchable.

5. The respiratory mask assembly of claim 4, wherein the annular portion is configured to encircle the occipital region of the head of the user.

6. The respiratory mask assembly of claim 3, wherein the headgear assembly further comprises a pair of upper side straps and a pair of lower side straps.

7. The respiratory mask assembly of claim 6, wherein the back strap, the top strap, the pair of upright straps, the pair of upper side straps, and the pair of lower side straps can be at least partially coupled together by ultrasonic welding.

8. The respiratory mask assembly of claim 6, further comprising a mask frame comprising headgear attachments, wherein the mask frame is configured to couple to the seal chamber.

9. The respiratory mask assembly of claim 8, wherein each of the pair of upper side straps and the pair of lower side straps comprise ends with fasteners that loop through a respective one of a plurality of headgear attachments on the mask frame and the fasteners are configured to couple with complementary fasteners on a side of the pair of upper side straps and a side of the pair of lower side straps.

10. The respiratory mask assembly of claim 8, wherein the headgear assembly is configured to directly couple to the maskframe.

11. The respiratory mask assembly of claim 3, wherein the top strap comprises a length adjuster.

12. The respiratory mask assembly of claim 2, wherein the headgear assembly comprises:
   a back strap which, in use, extends around a back of the head of the user at a location above a nape of a neck of the user but below an occipital protuberance;
   a pair of upper side straps;
   a pair of lower side straps which extend from the back strap at a location below a respective ear of the user to a location slightly forward of the respective ear, in use;
   a pair of upright straps which extend upward from the back strap at a location rearward of a respective ear of the user to a location above the respective ear, in use;
   a top strap which connects to the upper side straps at a location generally above a respective ear of the user, in use;
   wherein the back strap, the top strap and the pair of uprights straps form an annular shape which encircles the occipital protuberance, or upper rear portion, of the head of the user in use, and the annular shape comprises a three-dimensional shape.

13. The respiratory mask assembly of claim 1, wherein the fluid connector is an elbow.

14. The respiratory mask assembly of claim 1, wherein the releasable connection comprises a quick release button.

15. The respiratory mask assembly of claim 14, wherein the quick release button comprises the protrusion configured to engage the shoulder on the ball joint.

16. An air vent module for a mask assembly for use in administering continuous positive airway pressure treatment, the air vent module comprising:
- an annular component comprising a passage defined by a passage wall,
- a coupler configured to mate the annular component of the air vent module to a mask frame of the mask assembly, and
- a plurality of vent holes arranged in a circular configuration to provide radial diffusion of exhaust air; and
- a connection port assembly, the connection port assembly comprising:
  - a fluid connector,
  - a ball end at a first end of the fluid connector, the ball end comprising an outer surface that is contoured to be snap fit into the passage wall of the air vent module whereby a ball joint between the passage and the ball end allows the passage wall and the outer surface to slide relatively freely with each other such that an angle between the connection port assembly and a seal chamber can be changed,
  - a swivel connector at a second end of the fluid connector configured for connection to a conduit that is in fluid communication with a respiratory gases supply; and
  - wherein the fluid connector and the ball end are secured by engaging a protrusion on the fluid connector with a shoulder positioned at an internal surface of the ball end at a location directly inside an outer spherical surface of the ball end.

17. The air vent module of claim 16, wherein the fluid connector is an elbow comprising a bend of 90 degrees.

18. The air vent module of claim 16, wherein the swivel connector comprises a cylindrical inner component and a cylindrical outer component that slides over the cylindrical inner component to provide rotational movement of the cylindrical outer component.

19. The air vent module of claim 16, wherein the passage wall comprises a ball socket with a concave surface configuration.

20. The air vent module of claim 16, wherein the connection port assembly can rotate and have angular movement relative to the passage.

* * * * *